United States Patent
Katsumata et al.

(10) Patent No.: US 9,113,799 B2
(45) Date of Patent: Aug. 25, 2015

(54) RADIATION IMAGING APPARATUS AND IMAGING METHOD USING RADIATION

(75) Inventors: Akitoshi Katsumata, Ichinomiya (JP); Koichi Ogawa, Nakano-ku (JP); Tsutomu Yamakawa, Nishinomiya (JP); Masahiro Tsujita, Ikoma (JP); Tatsuya Nagano, Takatsuki (JP); Kazuhide Kitou, Mino (JP)

(73) Assignee: Telesystems Co., Ltd., Osaka (JP)

( * ) Notice: Subject to any disclaimer, the term of this patent is extended or adjusted under 35 U.S.C. 154(b) by 631 days.

(21) Appl. No.: 13/386,838

(22) PCT Filed: Jul. 29, 2010

(86) PCT No.: PCT/JP2010/062842
§ 371 (c)(1),
(2), (4) Date: Jun. 1, 2012

(87) PCT Pub. No.: WO2011/013771
PCT Pub. Date: Feb. 3, 2011

(65) Prior Publication Data
US 2012/0230467 A1  Sep. 13, 2012

(30) Foreign Application Priority Data
Jul. 30, 2009 (JP) .................................. 2009-178415

(51) Int. Cl.
*A61B 6/03* (2006.01)
*A61B 6/14* (2006.01)
*A61B 6/00* (2006.01)
(52) U.S. Cl.
CPC . *A61B 6/032* (2013.01); *A61B 6/14* (2013.01); *A61B 6/145* (2013.01); *A61B 6/501* (2013.01); *A61B 6/037* (2013.01); *A61B 6/466* (2013.01)
(58) Field of Classification Search
CPC ........ A61B 6/032; A61B 6/0478; A61B 6/14; A61B 6/4233; A61B 6/466; A61B 6/501
USPC ................................................. 378/38, 39, 40
See application file for complete search history.

(56) References Cited

U.S. PATENT DOCUMENTS 6,196,715 B1    3/2001  Nambu et al.
6,493,415 B1 *  12/2002  Arai et al. .......................... 378/4
(Continued)

FOREIGN PATENT DOCUMENTS

JP    57-203430 A    12/1982
JP    4-144548 A     5/1992
(Continued)

OTHER PUBLICATIONS

R. Molteni, "A universal test phantom for dental panoramic radiography," MedicaMundi, vol. 36, No. 3, 212-217 (1991).*
(Continued)

*Primary Examiner* — Allen C. Ho
(74) *Attorney, Agent, or Firm* — Harness, Dickey & Pierce, PLC

(57) ABSTRACT

There is provided a panoramic imaging apparatus which serves as a radiation imaging apparatus. The panoramic imaging apparatus includes an X-ray tube radiating an X-ray as a radiation, a detector outputting digital-quantity frame data corresponding to an incident X-ray, and moving means moving the pair of X-ray tube and the detector relatively to an object. The apparatus further includes means for acquiring the frame data from the detector during movement of the X-ray tube and the detector, and means for optimally focusing a portion being imaged of the object using the acquired data and producing a three-dimensional optimally focused image in which the real size and shape of the portion being imaged are reflected.

17 Claims, 26 Drawing Sheets

(56) References Cited

U.S. PATENT DOCUMENTS

| | | | |
|---|---|---|---|
| 6,570,953 B1 * | 5/2003 | Dobert et al. | 378/21 |
| 6,619,839 B2 * | 9/2003 | Yoshimura | 378/196 |
| 7,039,156 B2 * | 5/2006 | Arai et al. | 378/39 |
| 7,336,763 B2 * | 2/2008 | Spartiotis et al. | 378/40 |
| 7,347,622 B2 * | 3/2008 | Sadakane et al. | 378/197 |
| 7,421,059 B2 * | 9/2008 | Suzuki et al. | 378/39 |
| 7,424,091 B2 * | 9/2008 | Park et al. | 378/39 |
| 7,676,022 B2 * | 3/2010 | Pantsar et al. | 378/39 |
| 7,715,525 B2 * | 5/2010 | Spartiotis et al. | 378/39 |
| 7,742,560 B2 * | 6/2010 | Spartiotis et al. | 378/38 |
| 7,778,388 B2 | 8/2010 | Sendai | |
| 7,787,586 B2 * | 8/2010 | Yoshimura et al. | 378/4 |
| 7,876,878 B2 * | 1/2011 | Crucs | 378/39 |
| 7,916,833 B2 * | 3/2011 | Pantsar et al. | 378/38 |
| 7,978,813 B2 * | 7/2011 | Yoshimura | 378/38 |
| 8,005,187 B2 * | 8/2011 | Suzuki et al. | 378/39 |
| 8,300,762 B2 * | 10/2012 | Suzuki et al. | 378/39 |
| 8,433,033 B2 * | 4/2013 | Harata et al. | 378/38 |
| 8,503,603 B2 * | 8/2013 | Tancredi et al. | 378/39 |
| 8,588,364 B2 * | 11/2013 | Suzuki et al. | 378/40 |
| 2006/0203959 A1 | 9/2006 | Spartiotis et al. | |
| 2006/0277530 A1 | 12/2006 | Wu et al. | |
| 2008/0019477 A1 | 1/2008 | Spartiotis et al. | |
| 2008/0063139 A1 | 3/2008 | Pantsar et al. | |
| 2009/0123892 A1 | 5/2009 | Sogo et al. | |
| 2009/0310845 A1 | 12/2009 | Ogawa et al. | |
| 2010/0142673 A1 | 6/2010 | Pantsar et al. | |
| 2010/0208866 A1 | 8/2010 | Spartiotis et al. | |
| 2011/0019192 A1 | 1/2011 | Imura | |

FOREIGN PATENT DOCUMENTS

| | | | | |
|---|---|---|---|---|
| JP | 6-88790 A | | 3/1994 | |
| JP | WO 2007/046458 A1 * | | 4/2007 | A61B 6/14 |
| JP | 2007-136163 A * | | 6/2007 | A61B 6/14 |
| JP | 2008-86659 A | | 4/2008 | |

OTHER PUBLICATIONS

International Search Report for PCT/JP2010/062842, ISA/JP, mailed Nov. 2, 2010.

English Translation of the International Preliminary Report on Patentability, IB/Geneva, issued Feb. 7, 2012, incorporating the English Translation of the Written Opinion of the ISA, ISA/JP, mailed Nov. 2, 2010.

* cited by examiner

FIG.15(1)
(A)
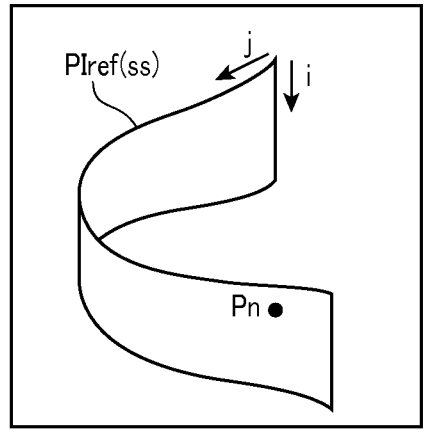
(B)
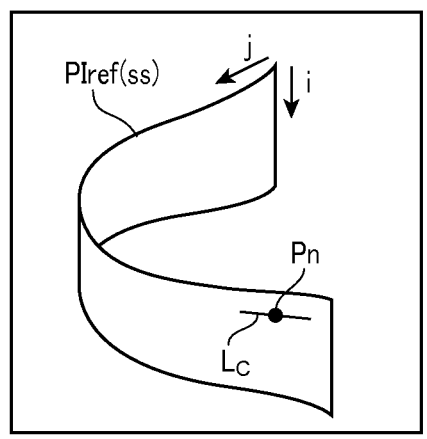
(C)
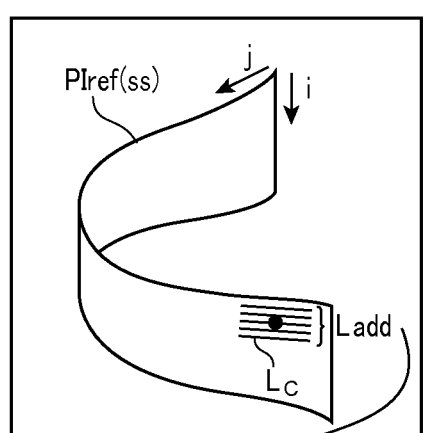
(D)
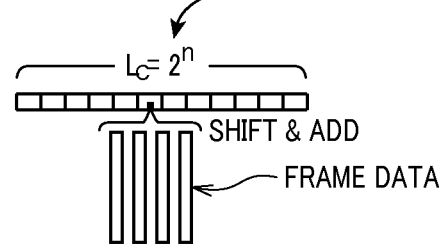

RADIATION IMAGING APPARATUS AND IMAGING METHOD USING RADIATION

CROSS-REFERENCE TO RELATED APPLICATION

This application is a 371 U.S. National Stage of International Application No. PCT/JP2010/062842, filed Jul. 29, 2010, which claims priority to Japanese Patent Application No. JP 2009-178415, filed Jul. 30, 2009. The disclosures of the above applications are entirely incorporated by reference herein.

BACKGROUND

1. Field of the Invention

The present invention relates to a radiation imaging apparatus and imaging method using the radiation, and in particular, to the radiation imaging apparatus and imaging method using the radiation in which and by which radiation data is obtained by radiation-scanning an object in plural directions, the obtained radiation data are processed with a tomosynthesis method to reconstruct topographic data, the reconstructed tomographic data being used to identify three-dimensional positions of internal structures of the object.

2. Background Art

In recent years, tomographic imaging using a tomosynthesis technique has been used actively. The theory of this tomosynthesis technique has been known long before (for example, refer to patent reference 1), and recently, tomographic imaging that enjoys ease of image reconstruction performed using the tomosynthesis technique has been proposed (for example, refer to patent references 2 and 3). Especially, many such cases can be found in dental and mammographic fields (for example, refer to patent references 4, 5 and 6).

In the dental field, tomosynthesis technique is usually put into practical use as a panoramic imaging apparatus that acquires panoramic images in which a curved tooth row is usually expanded into a two-dimensional plane. This panoramic imaging apparatus is usually provided with a mechanism that rotates a pair of an X-ray tube and an X-ray detector around the oral cavity of an object being imaged. The X-ray detector has pixels mapped in a rectangle of a portrait-oriented width. The mechanism rotates the pair of the X-ray tube and the X-ray detector with a rotation center thereof intricately so that the rotation center traces a predetermined orbit which is previously set along a tooth row. The predetermined orbit is set to focus on a 3D referential tomographic plane previously set along a tooth row which can be regarded as a tooth row having a standard shape and size. During the rotation, an X-ray beam is radiated from the X-ray tube at given intervals and the X-ray is transmitted through the object to be received by the X-ray detector, and digital frame data is detected from the detector. In this way, the frame data focusing on the 3D referential tomographic plane is acquired at the given intervals. These frame data are subjected to reconstruction using the tomosynthesis technique so as to provide a panoramic image of the 3D referential tomographic plane.

However, the foregoing conventional panoramic imaging apparatuses do not take it account the facts that there are differences between the tooth row of each object and the 3D referential tomographic plane and positioning tooth rows involves difficult operations. As might be expected, there are individual differences in the shapes and sizes of the tooth rows of respective objects. The sizes of objects' jaws differ depending on the individuals, making it difficult to correctly position the tooth rows. This often causes defocused panoramic images to be reconstructed, which may fail to meet a demand for fine interpretation of the images. In such cases, if it is desired to finely examine cases including cavities and alveolar pyorrhea, it is needed to perform intraoral imaging or dental CT imaging, separately from the panoramic imaging. Re-performance of the panoramic imaging and X-ray imaging using another modality will raise the amount of X-rays to which the object is exposed.

In order to try to overcome such difficulties, there is provided an apparatus provided by patent reference 7. In the panoramic imaging apparatus shown in this publication, a phantom is used to previously measure gains (i.e., distance information for mutual addition of frame data) and positions in each of depth directions of a tooth row. Additionally, acquired frame data are used to produce a focus-optimized image of the 3D referential tomographic plane using the tomosynthesis technique. In the focus-optimized image, a ROI is set to specify a partial region, and a focus-optimized image at a selected position in the front-back direction (i.e., each of front-back directions of the tooth row, which connect the X-ray tube and the X-ray detector at each of the radiation positions) of the partial region are reconstructed using already acquired frame data and a gain necessary among the gains which have been measured. Hence, the data acquisition is performed one time with the 3D referential tomographic plane focused, and then, a focus-optimized image of any partial region can be reconstructed by making use of the already acquired frame data.

PRIOR ART REFERENCE

Patent Reference

[Patent Reference 1] JP-A-S57-203430
[Patent Reference 2] JP-A-H6-88790
[Patent Reference 3] JP-A-H10-295680
[Patent Reference 4] JP-A-H4-144548
[Patent Reference 5] JP-A-2008-110098
[Patent Reference 6] US2006/0203959 A1
[Patent Reference 7] JP-A-2007-136162

However, the panoramic imaging apparatus provided by the patent reference 7 does not consider the fact that teeth being imaged are curved or warped in their longitudinal directions. It is usual that each tooth of a tooth row is not at the same longitudinal position. It is frequent that the teeth are curved inwards in the oral cavity as advancing to the base thereof. It is thus difficult to focus on all the areas of each tooth on one section. With consideration of this regard, it is necessary to focus on all the longitudinal areas of the teeth to raise depiction performance thereof. In other words, though the foregoing panoramic imaging apparatus can focus on any partial region located at an arbitrary position in the front-back direction, it is difficult to obtain one panoramic image which is focused through the entire areas of a tooth row. Even when best-focused partial images are connected to represent an entire panoramic image, there are caused irregularities between connected edges of the partial images, thus spoiling the connection.

The foregoing difficulty is boosted by the fact that enlargement factors in the longitudinal and lateral directions of an image (i.e., the longitudinal and width directions of the tooth row) differ depending on changes in the rotation center position during the scanning. The enlargement factor is defined as a ratio between the actual size of a tooth and the size of an enlarged image of the tooth, of which shadow is projected to the X-ray incident surface of the X-ray detector. Since the X-ray tube has an X-ray source which is small enough which can be regarded as a point source, the X-rays are radiated from the point X-ray source. However, in reconstructing a tooth row in a 3D tomographic plane based on the tomosynthesis technique, the lateral enlargement of a reconstructed image is the same at any positions on the image, but the longitudinal enlargement thereof differs at the positions. This causes a panoramic image to be reconstructed longer than the actual size of a tooth row in the lateral direction. In addition, the enlargement, that is, the degree by which an image is longer longitudinally, differs depending on where a tooth is located, i.e. in the anterior teeth or both side molar teeth (i.e., back teeth), causing the longitudinal shapes thereof depending on the tooth is an anterior or molar teeth, thus causing distortion among the teeth in a panoramic image. Still more, when a tooth row is not entirely or partially along a given 3D referential tomographic plane, the distortion among respective portions of the tooth row will be enhanced more severely due to differences in the longitudinal and lateral directions.

In the conventional panoramic imaging apparatus in which digital-quantity frame data are acquired to reconstruct a panoramic image thereon, post processing is often carried out to remedy the foregoing difficulty. In this post processing, a reconstructed image is multiplied by coefficients which allow the sizes of the teeth to be shortened such that the ratio between the longitudinal and lateral enlargements becomes the same, at least, at the center of the anterior teeth area. Even in such a remedy, the height of the molar teeth is depicted smaller than the actual size thereof in the panoramic image. That is, there remains distortion among the individual teeth due to the fact that the enlargement factor differs positionally.

In this way, the difficulty resulting from differences of the enlargement factor has not been overcome, and optimally focusing on the entire region of an object in a panoramic image has not been realized. It is thus frequently difficult to interpret and diagnose teeth and/or the gum depicted in the conventional panoramic image. Particularly it is difficult to reliably measure lengths and distances in such images. Hence, for instance, implant placement is confronted with a difficulty of positioning implanted portions with less accuracy.

As a conventional countermeasure, a marker to indicate a reference position is attached to a desired position in the oral cavity before imaging, so that the reference position is given in an image. With reference to the reference position, the image is corrected to maintain accuracy, so that the foregoing difficulty is compensated as much as possible. However, in this measure, steps for imaging and diagnosis become complex. An operational burden on operators is heavier. Thus, due to such reasons, the marker cannot be used easily for preventive practice such a screening test. It is therefore highly needed to provide panoramic images which can be used widely from the preventive measure such as screening to complicated treatment such as implant placement.

In addition, a three-dimensional panoramic image would be useful for diagnosing the whole structure of a tooth row in its back-and-forth direction. However, images which meet such a need and overcome the freeing various difficulties have not been provided yet.

In consideration of the foregoing, it is an object of the present invention to provide a radiation imaging technique which is able to optimally focus on the entire region of an object being imaged in a three-dimensional panoramic image in a state where the actual state (position and shape) of the object is three-dimensionally depicted with higher accuracy and distortion due to changes in the enlargement factor is removed or reduced well.

SUMMARY

In order to achieve the object, the present invention provides a radiation imaging apparatus, a data processing apparatus, an imaging method using the radiation, and a computer program.

Of these, a radiation imaging apparatus, characterized in that the apparatus includes a radiation emitting source that emits a radiation; a radiation detector that output, frame by frame, digital-quantity two-dimensional data corresponding to incidence of the radiation thereto; moving means for moving a pair of the radiation emitting source and the radiation detector, the radiation detector, or an object being imaged relatively to a remaining one among the radiation emitting source, the radiation detector, and the object; data acquiring means for acquiring, frame by frame, the data outputted from the radiation detector while the pair of the radiation emitting source and the radiation detector, the radiation detector, or the object is moved relatively to the remaining one by the moving means; and image producing means for producing a three-dimensional optimally focused image based on the data acquired by the data acquiring means, a portion to be imaged of the object in the three-dimensional optically focused image being optimally focused and reflecting an actual size and shape of the portion thereon.

Further, the data processing apparatus processing data outputted from a system comprising: a radiation emitting source that emits a radiation; a radiation detector that output, frame by frame, digital-quantity two-dimensional data corresponding to incidence of the radiation thereto; moving means for moving a pair of the radiation emitting source and the radiation detector, the radiation detector, or an object being imaged relatively to a remaining one among the radiation emitting source, the radiation detector, and the object; and data acquiring means for acquiring, frame by frame, the data outputted from the radiation detector while the pair of the radiation emitting source and the radiation detector, the radiation detector, or the object is moved relatively to the remaining one by the moving means, characterized in that the data processing apparatus comprises: data storing means for receiving and storing therein the data; and image producing means for producing a three-dimensional optimally focused image based on the data stored in the data storing means, a portion to be imaged of the object being imaged to be optimally focused and to reflect an actual size and shape of the portion thereon.

In addition, the method of imaging using a radiation, characterized in that the method comprises steps of: acquiring data, frame by frame, outputted from a radiation detector while a pair of the radiation emitting source and the radiation detector, the radiation detector, or an object being imaged is relatively moved relatively to a remaining one among the radiation emitting source, the radiation detector, and the object, the radiation detector outputting, frame by frame, digital-quantity two-dimensional data corresponding to incidence of the radiation thereto; and producing a three-dimensional optimally focused image based on the data acquired by the acquiring step, a portion to be imaged of the object in the three-dimensional optically focused image being optimally focused and reflecting an actual size and shape of the portion therein.

The computer-readable program stored in a memory and readable from the memory by a computer and produced to enable the computer to process data outputted from a system comprising: a radiation emitting source that emits a radiation; a radiation detector that output, frame by frame, digital-quantity two-dimensional data corresponding to incidence of the radiation thereto; moving means for moving a pair of the radiation emitting source and the radiation detector, the radiation detector, or an object being imaged relatively to a remaining one among the radiation emitting source, the radiation detector, and the object; and data acquiring means for acquiring, frame by frame, the data outputted from the radiation detector while the pair of the radiation emitting source and the radiation detector, the radiation detector, or the object is moved relatively to the remaining one by the moving means, characterized in that the program enables the computer to have functions realized by steps of: reconstructing, as a referential-plane image, a projection image produced by projecting a desired referential tomographic plane of a portion being imaged of the object to a detection surface of the radiation detector based on the data acquired; setting a plurality of tomographic planes along the 3D referential tomographic plane in a direction opposed to the 3D referential tomographic plane; calculating pixel values of each of the plurality of tomographic planes based on pixel values of the referential tomographic plane; identifying optimally focused sampling points of the portion being imaged based on image data of both the 3D referential tomographic plane and the plurality of tomographic planes to which the pixel values are provided; providing the identified sampling points with pixel values based on the pixel values at the sampling points corresponding to the panoramic image and being present in a viewing direction from the X-ray tube to the detector via the respective sampling points; deciding the portion being imaged, by recognizing the 3D referential tomographic plane provided at the sampling points to which the pixel values are provided and a characteristic pattern shown by pixel values of the plurality of tomographic planes; removing noise from the sampling points of the decided portion being imaged; and producing a three-dimensional optimally focused image including the portion being imaged with an actual size and shape of the portion reflected thereon, by connecting the sampling points of the portion from which the noise is removed.

Effects of the Invention

According to the radiation imaging apparatus, the data processing apparatus, the imaging method using the radiation, and the computer program, acquired data are used to provide a three-dimensional optimally focused image in which a portion being imaged of an object is optimally focused and imaged to have an actual size and shape reflected thereon. That is, with the actual state (position and size) of the portion depicted three-dimensionally with accuracy, the entire image is optimally focused and is removed or reduced from being distorted due to differences of the enlargement factor.

BRIEF DESCRIPTION OF THE DRAWINGS

FIG. 15(2) is a view explaining, together with FIG. 15(1), the process to identify optimally-focused tomographic planes for each of positions on the 3D reference image;

DETAILED DESCRIPTION OF PREFERRED EMBODIMENTS

With reference to the accompanying drawings, embodiments of the present invention will now be described.

Referring to FIGS. 1-29, an embodiment of a three-dimensional position identifying apparatus, a radiation imaging apparatus and an imaging method using radiation, which are according to the present invention, will now be described. These apparatuses and method are put into practice as a dental panoramic imaging apparatus that uses X-rays (X-ray beams). This panoramic imaging apparatus will now be described.

Figure 1:
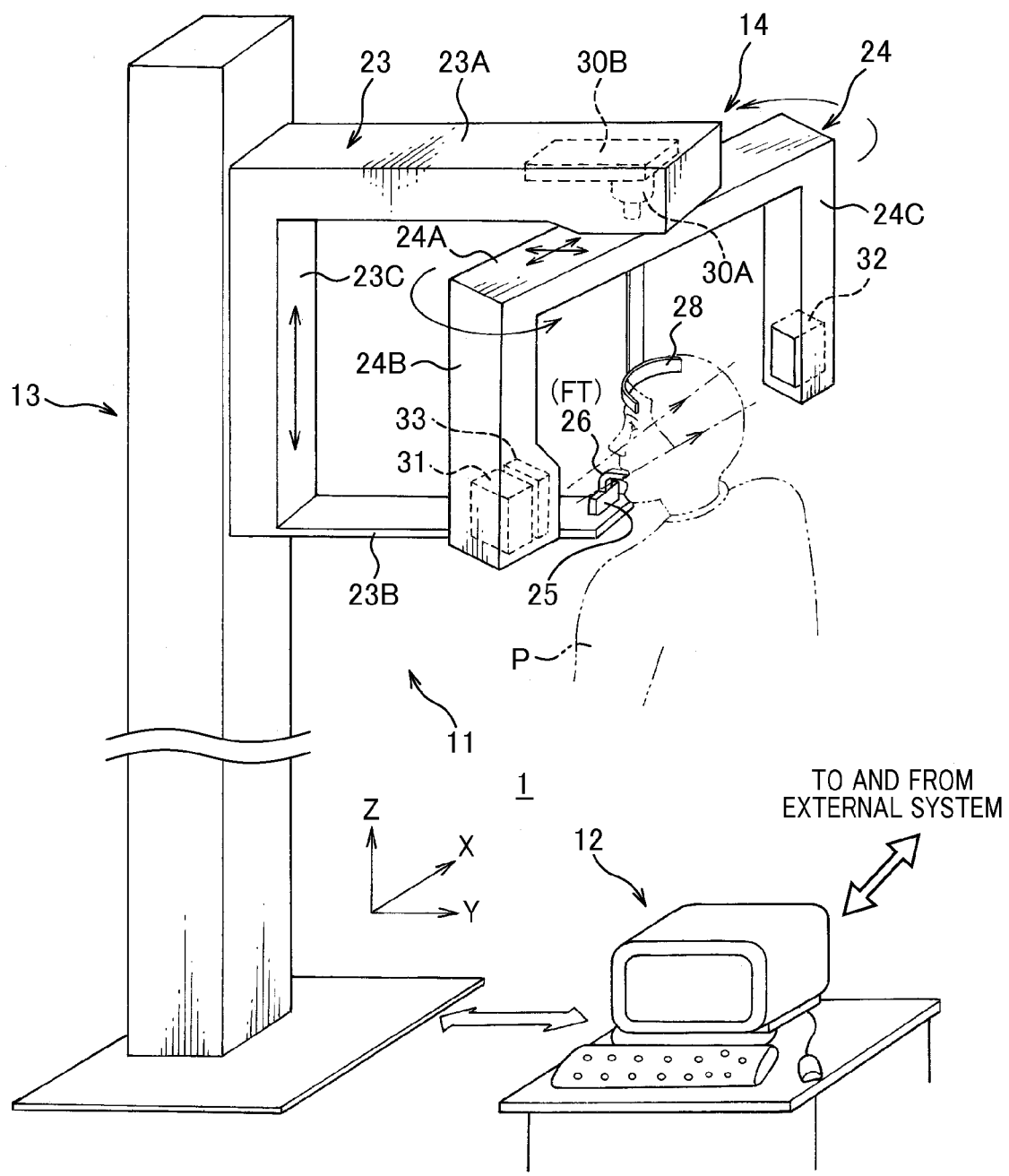
FIG. 1 is a perspective view outlining the whole configuration of an X-ray panoramic imaging apparatus employed as a radiation imaging apparatus according to one embodiment of the present invention.

FIG. 1 outlines the appearance of the panoramic imaging apparatus 1. This panoramic imaging apparatus 1 is able to scan, with an X-ray beam, the jaw of an object to obtain digital X-ray transmission data, and use the data to specify a real position (i.e., actual position) of the tooth row of a three-dimensional structure in the jaw and to produce a panoramic image of the tooth row whose irregularities (or differences) caused due to a later-described enlargement factor are compensated. In addition to this basic performance, the panoramic imaging apparatus 1 is able to provide breakthrough features such as various modes of display and measurements based on such panoramic images. Additionally this imaging apparatus can reduce an amount of X-ray exposure to objects being imaged and provide operators with good usability. The foregoing basic performance is obtained by using a tomosynthesis technique.

The configuration of this panoramic imaging apparatus 1 will now be outlined. As shown in FIG. 1, this apparatus 1 is provided with a gantry 11 with which data is acquired from an object (patient) P who is in a standing position, for example, and a control & calculation apparatus 12 realized by use of a computer. The control & calculation apparatus 12 is configured to control data acquisition performed by the gantry 11, produce panoramic images based on the acquired data, and post-process the panoramic images in an interactive or manual manner with an operator (doctor or medical operator).

The gantry 11 has a standing unit 13 and an imaging unit 14 movable upward and downward relative to the standing unit 13. The imaging unit 14 is attached to the pillar of the standing unit 13 to be movable upward and downward in a predetermined range.

For the sake of easier explanation, the panoramic imaging apparatus is given the XYZ orthogonal coordinate system whose Z-axis is assigned to the longitudinal direction, i.e., the vertical direction, of the standing unit 13. Incidentally, a two-dimensional panoramic image, described later, is represented with its abscissa axis defined as a j-axis and its ordinate axis defined as an i-axis (i.e, Z-axis).

The imaging unit 14 includes a vertical movement unit 23 whose side appearance is approximately C-shaped and a rotation unit 24 rotatably (turnably) supported by the vertical movement unit 23. The vertical movement unit 23 is movable in a given range of height in the Z-axis direction (longitudinal direction) by a not-shown vertical movement mechanism (for example, a motor and a lack/pinion device) arranged in the standing unit 13. A command for this movement is provided from the control & calculation apparatus 12 to the vertical movement mechanism.

As described, the vertical movement unit 23 has a side appearance which is approximately C-shaped, and an upper arm 23A and a lower arm 23B located on the upper and lower sides respectively and a longitudinal arm 23C integrally connecting the upper and lower arms 23A and 23B. The longitudinal arm 23C is movably, in the vertical direction, supported on the foregoing standing unit 13. Of these arms 23A-23C, the upper arm 23A and the longitudinal arm 23C cooperatively provide an imaging space (real space). Inside the upper arm 23A, a rotary drive mechanism 30A for rotary drive (for example, an electric motor and a reduction gear) is arranged. The rotary drive mechanism 30A receives a command for rotary drive from the control & calculation apparatus 12. This rotary drive mechanism 30A has an output shaft, which is the rotation shaft of the electric motor, arranged to protrude from the upper arm 23A downward (downward in the Z-axis direction). To this rotation shaft, the rotation unit 24 is rotatably coupled. That is, the rotation unit 24 is arranged downward from the vertical movement unit 23, and rotates responsively to the drive of the rotary drive mechanism 30A.

The rotary drive mechanism 30A is linked with a movement mechanism 30B. This movement mechanism 30B is composed of devices such as a not-shown electric motor and gears. This movement mechanism 30B is also driven responsively to a command for rotary drive from the control & calculation apparatus 12, and is capable of moving the rotary drive mechanism 30A, i.e., the rotation unit 24 along the X-Y plane. Hence, the rotation center of a pair of an X-ray tube and a detector, which will be described later, can be moved to two-dimensionally trace a later-described trajectory which is along a given orbit in a predetermined range of the X-Y plane.

Meanwhile, the lower arm 23B extends to have a predetermined length in the same direction as that of the upper arm 23A. A chin rest 25 is placed on a tip end of the lower arm. A bite block 26 (or simply bite) is detachably attached to the chin rest 25. An object P, i.e., patient, bites the bite block 26, so that the chin rest 25 and the bite block 26 provide a function of positioning the oral cavity of the objet P.

The rotation unit 24 has also an approximately C-shaped appearance when being viewed from one side thereof in its used state, where the rotation unit 24 is rotatably attached to the motor output shaft of the upper arm 23A, with its opened end side directed downward. Practically, the rotation unit 24 has a lateral arm 24A rotatable (turnable) parallel with the lateral direction, that is, the X-Y plane and right and left vertical arms (the first and second vertical arms) extending downward (in the Z-axis direction) from both ends of the lateral arm 24A. The lateral arm 24A and the first and second vertical arms 24B and 24C, which are the right and left arms, are located within the imaging space (the real space), and driven to operate under the control of the control & calculation apparatus 12.

At an inner lower end of the first vertical arm 24B, an X-ray tube 31 is provided which functions as a radiation emitting source. This X-ray tube 31 is for example a rotating anode X-ray tube and has a target (anode) which radially emits X-rays toward the second vertical arm 24C. The focus of an electron beam made to collide with the target is as small in radius as 0.5-1 mm, that is, the X-ray tube 31 has a point X-ray source. On the X-ray output side of the X-ray tube 31, there is provided a collimator 33 having a slit. This slit collimates a comparatively thin beam-shaped X-ray, which is incident to the detector 32, to an actual acquiring window (for example, a window whose width is 5.0 mm) of the detector 32. Elements that compose the radiation emitting source may include this collimator 33.

In contrast, at an inner lower end of the second vertical arm 24C, there is provided, as a radiation detecting means, a digital type of X-ray detector 32 equipped with X-ray detection elements two-dimensionally arrayed (for example, arrayed in a matrix of 64×1500) and produced to detect the incident X-rays through the incidence window. By way of example, this detector 32 has a longitudinally-long shaped detecting portion (for example, 6.4 mm width×150 mm long) which is made of CdTe. In the present embodiment, since the tomosynthesis technique is adopted, it is indispensable to provide the detector 32 with a plurality of X-ray detecting elements in its lateral (width) direction.

The detector 32 is arranged such that its longitudinal direction agrees with the Z-axis direction. The detector 32 has a lateral effective width which is set to, for example, approximately 5.0 mm by the foregoing collimator 33. This detector 32 is capable of acquiring digital image data in accordance with amounts of incident X-rays at a frame rate of, for example, 300 fps (for example, 64×1500 pixels per frame). The acquired data are called "frame data."

Figure 2:
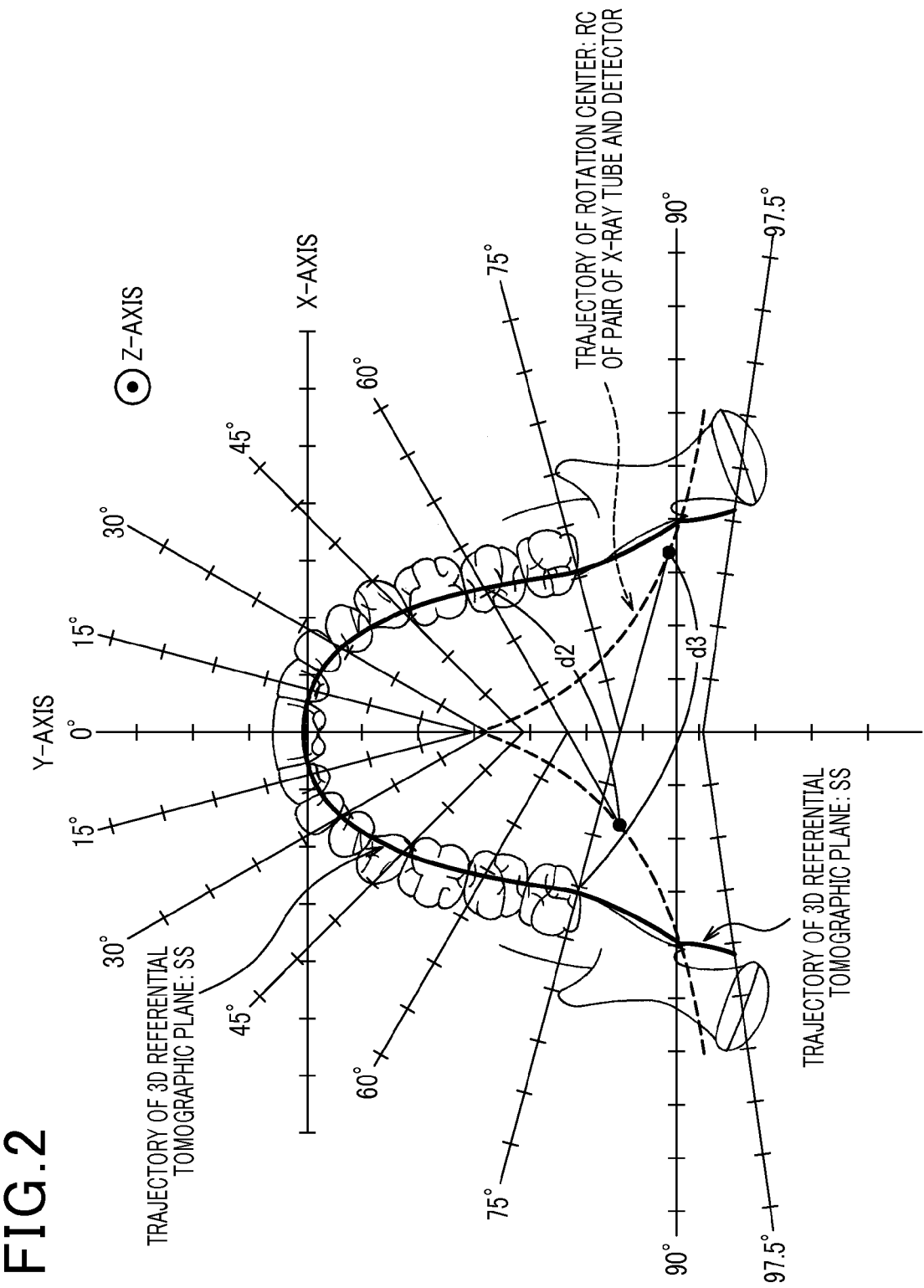
FIG. 2 is a view explaining the tooth row of an object being examined by the panoramic imaging apparatus according to the embodiment, a 3D referential tomographic plane which is set at the tooth row, and a trajectory of a rotation center on which a pair of an X-ray tube and a detector rotates.

During imaging, the X-ray tube 31 and the detector 32 are located to be opposed to each other with the oral cavity of the object P therebetween, and driven to rotate together as paired devices around the oral cavity. However, the rotation is not a rotation to draw a simple circle, and the pair of the X-ray tube 31 and the detector 32 is driven such that the rotation center RC of the pair traces a given chevron-shaped orbit consisting of two connected arcs inside an approximately horseshoe-shaped tooth row, as shown in FIG. 2. This given orbit is an orbit previously designed to enable the X-ray to focus on a section taken along a standard shape and size of the tooth row in the oral cavity (hereinafter, such a section is referred to as a 3D reference tomographic plane SS) and trace the 3D referential tomographic plane SS. When the X-ray is focused to trace the 3D referential tomographic plane SS, the X-ray tube 31 and the detector 32 are not always rotate at an equal angular speed to the 3D referential tomographic plane SS. This rotation can be a rotation referred to as "movement along the tooth row", in which the angular speed is changed arbitrarily during the rotation.

It is necessary that the X-ray tube 31 and the detector 32 should be moved to be opposed to each other and keep the oral cavity of the object P located between such devices. However this opposed attitude does not always require the X-ray tube 31 and the detector 32 to be directly opposed to each other. Depending on how to design the apparatus, the X-ray tube 31 and the detector 32 rotate independently of each other and, though the oral cavity of the object P should be located therebetween, the X-ray is radiated obliquely to the object.

The 3D referential tomographic plane SS presents an approximately horseshoe-shaped trajectory on the X-Y plane, i.e., when being viewed in the Z-axis direction, as described, and an example of such a trajectory is shown in FIG. 2. The trajectory of this 3D referential tomographic plane SS is also known from, for example, a paper "R. Molteni, "A universal test phantom for dental panoramic radiography" MedicaMudi, vol. 36, no.3, 1991." Information indicative of spatial positions defining this 3D referential tomographic plane SS is stored in a ROM 61 in advance.

Incidentally, although the 3D referential tomographic plane SS can be set as a known plane, this plane may be set to be according to each patient in advance. As such a setting technique, a camera is used to obtain a surface image of an object and the surface image is used to produce a desired three-dimensional section, medical modalities such as an MRI (magnetic resonance imaging), a CT (computed tomography) scanner, and an ultrasound diagnostic apparatus are used to image a patient's desired three-dimensional section, or three-dimensional data of a patient which are imaged by such medical modalities are used to obtain a desired three-dimensional section. Any of such sections can be used as a 3D referential tomographic plane. The 3D referential tomographic plane SS may be set using known techniques as above, and data showing the plane may be stored in the ROM 61 in advance.

Figure 3:
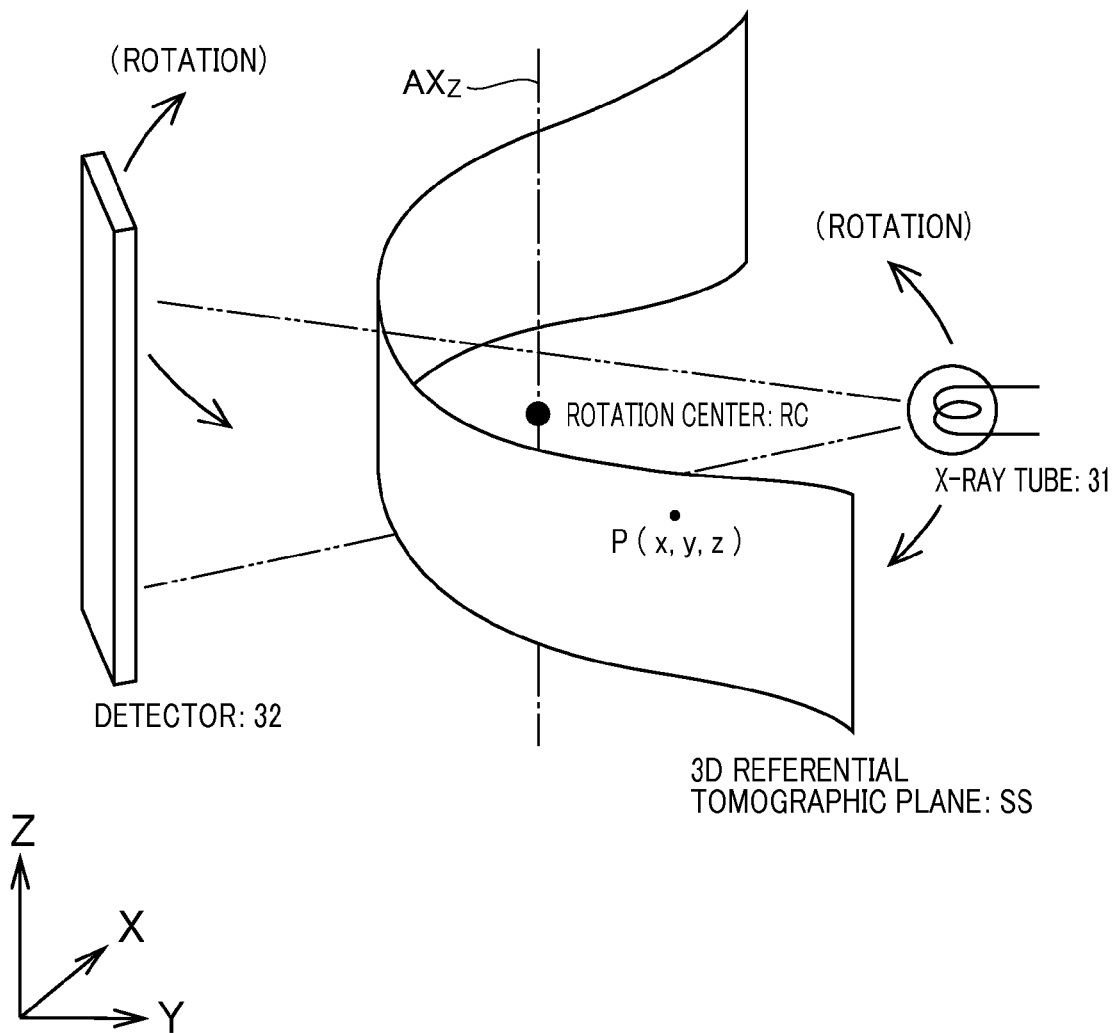
FIG. 3 is a perspective view explaining a geometry of the X-ray tube, the 3D referential tomographic plane, and the detector in the panoramic imaging apparatus.

The X-ray tube 31, the 3D referential tomographic plane SS, the detector 32, a rotation axis AXz, and the rotation center RC through which the rotation axis AXz passes have a geometrical positional relationship shown in FIG. 3. The 3D referential tomographic plane SS is parallel with the incident window of the detector 32 (the window is an X-ray detecting plane Ldet: refer to FIG. 6) and is a section curved along the Z-axis direction. This plane SS is defined as an elongated rectangular section when being developed two-dimensionally.

Figure 4:
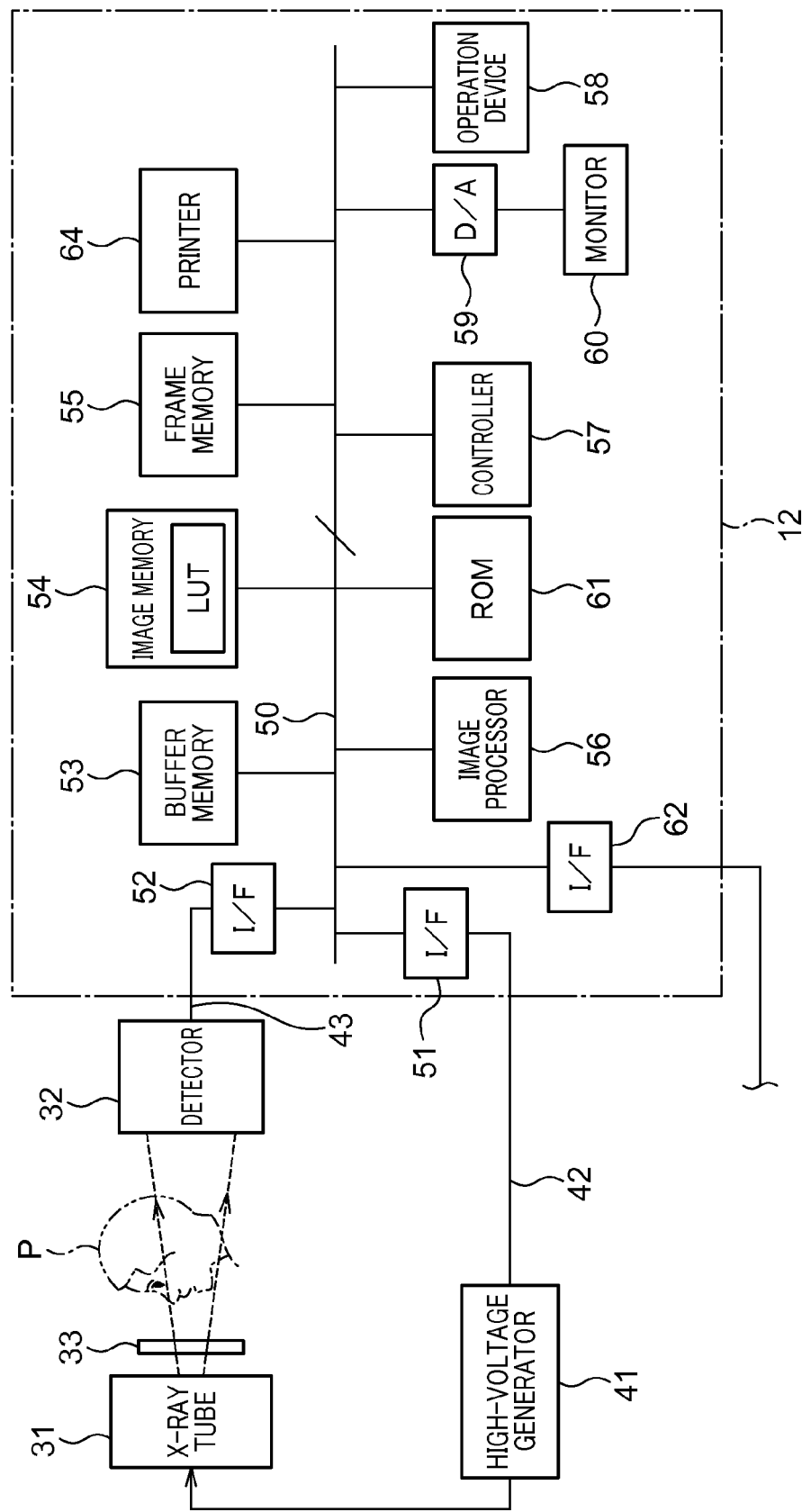
FIG. 4 is a block diagram outlining the electrical and electronic configuration of the panoramic imaging apparatus.

FIG. 4 shows an electric block form for control and processing performed by this panoramic imaging apparatus. As shown in the figure, the X-ray tube 31 is connected to the control & calculation apparatus 12 via a high-voltage generator 41 and a communication line 42. The detector 32 is connected to the control & calculation apparatus 12 via a communication line 43. The high-voltage generator 41 is arranged at the standing unit 13, the vertical movement unit 23, or the rotation unit 24 and responds to a control signal from the control & calculation apparatus 12 to be controlled according to X-ray radiation conditions such as a tube current and a tube voltage to the X-ray tube 31 and a timing sequence for the radiation.

The control & calculation apparatus 12 is required to process large amounts of image data, and is composed of for example a personal computer which is capable of storing large amounts of image data. The control & calculation apparatus 12 includes, as its essential components, interfaces 51, 52 and 62, a buffer memory 53, an image memory 54, a frame memory 55, an image processor 56, a controller (CPU) 57, and a D/A converter 59, which are mutually communicably connected via an internal bus 50. The controller 57 is communicably connected to an operation device 58, and the D/A converter 59 is also connected to a monitor 60. A printer 64 is also communicably connected to the internal bus 50.

Of the above components, the interfaces 51 and 52 are connected to the high-voltage generator 41 and the detector 32 respectively, and responsible for conducting communication on control information and acquired data transmitted from/to the controller 57 and to/from the high-voltage generator 41 and detector 32. The other interface 62 connects the internal bus 50 and a communication line, which allows the controller 57 to be communicable with an external apparatus. It is therefore possible that the controller 57 takes in oral images acquired by an external oral X-ray imaging apparatus and outputs panoramic images acquired by the present apparatus, to an external server based on for example DICOM (Digital Imaging and Communications in Medicine) protocol.

The buffer memory 53 temporarily stores digital-quantity frame data received from the detector 32 via the interface 52.

The image processor 56, which is under the control of the controller 57, has functions of producing panoramic images of a predetermined 3D referential tomographic plane provided by the apparatus itself and performing post-processes to utilize the panoramic images in an iterative manner with an operator. Programs for realizing such functions are stored in the ROM 61 in advance. Hence, the ROM 61 serves as a recording medium in which programs according to the present invention are stored. While such programs can be stored in the ROM 61 in advance as stated above, they can be installed into recording mediums such as a not-shown RAM, via a communication line or a portable memory from an external system in some cases.

In the present embodiment, the 3D referential tomographic plane is prepared previously by the apparatus. Alternatively, the 3D referential tomographic plane may be provided by selecting a desired one from plural tomographic planes prepared previously by the apparatus before performing imaging. In other words, the 3D referential tomographic plane is a fixed section in the imaging space, but the foregoing selection allows the plane to be movably positioned in a limited amount of range in the depth (back-and-forth) direction of a tooth row.

Frame data to be processed or processed now by the image processor 56 and image data are stored in the image memory 54 in a readable and writable manner. The image memory 54 is composed of for example a large-capacity recording medium such as a hard disc (nonvolatile and readable and writable). The frame memory 55 is used to display image data such as panoramic image data reconstructed and panoramic imager data to be post-processed. The image data being stored in the frame memory 55 are read at intervals from the D/A converter 59 to be converted into corresponding analog signals, and displayed on the monitor 60.

The controller 57 controls the operations of all the components of the apparatus based on programs for control and processing, which are previously stored in the ROM 61. The programs are set such that the controller 57 receives interactively information showing operator's operations for respective control items. Hence, the controller 57 is able to command acquisition (scanning) of frame data or other operations, as will be described later.

As shown in FIG. 1, a patient poses in a standing position or a seated position with his or her chin seated on the chin rest 25, his or her mouth biting the bite block 26, and his or her head touched to a head rest 28. This allows the patient's head (jaw) to be fixed positioned in an approximately central part in the space in which the rotation unit 24 rotates. With this patient's fixed posture, under the control of the controller 57, the rotation unit 24 rotates around the patient's head along the X-Y plane and/or an oblique plane to the X-Y plane (refer to arrows shown in FIG. 1).

During the rotation, under the control of the controller 57, the high-voltage generator 41 supplies to the X-ray tube 31 a pulse-mode high voltage (designated tube voltage and tube current) at intervals, whereby the X-ray tube 31 is driven on the pulse mode. This allows the X-ray tube 31 to radiate pulsed X-rays at intervals. The X-rays are transmitted through the patient's jaw (including the tooth row portion) positioned at the designated imaging position) and enters the detector 32. Responsively to this, the detector 32 detects the incident X-rays at a very fast frame rate (for example 300 fps) as described, and outputs in sequence, frame by frame, corresponding electric-quantity two-dimensional frame data (for example 64×1500 pixels). The outputted frame data are transmitted to the buffer memory 53 via the communication line 43 and the interface 52 in the control & calculation apparatus 12 for temporal storage therein. The frame data in the buffer memory 53 are then transferred to the image memory 54 for storage therein.

Hence, the image processor 56 is configured to reconstruct (produce), as a panoramic image (a referential panoramic image), a tomographic image that focuses the 3D referential tomographic plane SS using the frame data stored in the image memory 54. That is, this referential panoramic image is defined as "a panoramic image obtained under an assumption that a tooth row is present at and along the 3D referential tomographic plane SS." In addition, the image processor uses this referential panoramic image to produce a three-dimensional (3D) referential image and a three dimensional (3D) autofocus image. This processing is outlined in FIG. 5. The 3D referential image is defined as "a three-dimensional image obtained under an assumption that a tooth row is present at and long the 3D referential tomographic plane SS." The 3D autofocus image is defined as "a surface image (i.e., a pseudo 3D surface image) automatically optimally focusing on the tooth row from the 3D referential image using frame data or data of the referential panoramic image." In other words, the 3D autofocus image is a surface image with less blur and optimally focused, where the real position and actual size of a tooth row is depicted with higher precision.

In particular, it can be said that the 3D autofocus image takes into consideration that 3D autofocus images of individual persons differ person by person in most cases. In practice, it is very rare to find that tooth rows of individual persons being imaged are at and along the 3D referential tomographic plane SS (refer to FIG. 6). The tooth rows may partially or entirely offset from the 3D referential tomographic plane SS or may be oblique to that plane. In light of this, the 3D autofocus image is produced by automatically and accurately identifying the actual three-dimensional spatial position and shape of the tooth row of each person being imaged and automatically extracting from the identified results the actual shape of the person's tooth row.

Figure 6:
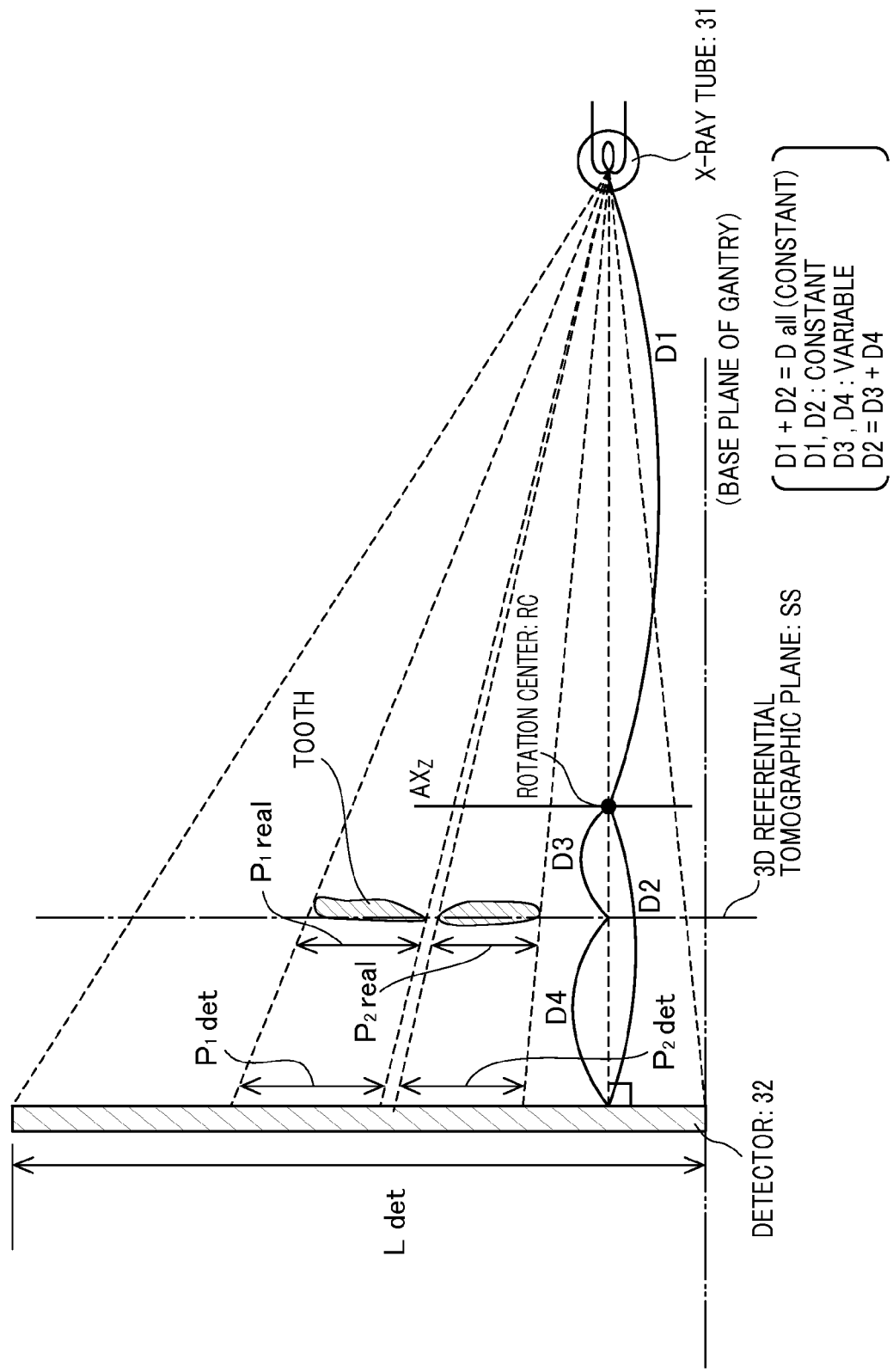
FIG. 6 is a view explaining a positional relationship among the X-ray tube, the 3D referential tomographic plane, the rotation center, and the detector.

The X-rays radiated from the X-ray tube 31 (serving as a point X-ray source) are transmitted through the oral cavity of an object P, and then are detected by the long detector 32 having a certain length in the X-axis direction. Hence, the radiated directions of the X-rays are oblique, as shown in FIGS. 3 and 6. Accordingly, there exists a ratio between the actual size of the tooth and the size of an image produced by the shade of the tooth projected onto the X-ray incident surface Ldet of the detector 32, and this ratio changes depending on positions of the rotation center RC. In the present embodiment, this ratio is called "an enlargement factor." In the example shown in FIG. 6 (only the height of the tooth is explained), a ratio between the actual height $P1_{real}$ of the tooth and the height $P1_{det}$ on the X-ray incident surface Ldet changes depending on positions of the rotation center RC. As exemplified in FIG. 2, the rotation center RC takes various positions, which change during one scan (data acquisition). An orbit on which the positions trace is set previously. The reason for the orbit is follows. As shown in FIG. 6, a distance Dall between the X-ray tube 31 and the detector 32 is kept unchanged, and distances D1 and D2 from the rotation center RC to the X-ray tube 31 and the detector 32 respectively are also kept unchanged. Meanwhile, for scanning with focusing on the 3D referential tomographic plane SS, design is made such that, during one scan, the orbit traced by the positions of the rotation center RC changes to depict, by way of example, the shape of a mountain (refer to FIG. 2) to the horseshoe-shaped curved tooth row.

Concretely, a distance D3 from the rotation center RC to the 3D referential tomographic plane SS and a distance D4 (D3+D4=D2) from the detector 32 to the 3D referential tomographic plane SS change depending on advancement of the scanning. Depending on these changes, the rotation center RC comes closer to recedes from the tooth row, so that the X-ray tube 31 comes closer to or recedes from the tooth row as well. Since the X-ray tube 31 has an X-ray source which can be regarded as a point source, the size of a projection image onto the detection surface Ldet becomes bigger as the X-ray tube 31 comes closer to the tooth row even under a condition where the height of the tooth is the same. That is, the enlargement factor becomes larger in such a case. In the example shown in FIG. 2, compared with a case where the molar teeth are scanned, scanning the anterior teeth allows the rotation center RC to come closer to the tooth row, providing the enlargement factor with larger amounts depending on how much closer to the tooth row. For example, in the case of FIG. 2, the distance d1 is given when one of the anterior teeth is scanned in an X-ray radiation direction of 0 degrees for example. Meanwhile, in the case of scanning some of the molar teeth, there are provided distances d2 and d3 in the X-ray radiation directions of 60 degrees and 75 degrees respectively, for example. In this example, there are provided relationships of d1<d2, d1<d3, and d2<d3. Although the trajectory of the rotation center RC shown in FIG. 2 is simply an example, it is always true that the rotation center RC comes closer to and then gets away from the tooth row when scanning is made to focus on the 3D referential tomographic plane SS by the panoramic imaging apparatus.

In such a case, the enlargement factor changes depending on what part of the tooth row is scanned. This fact becomes a significant barrier in an attempt at quantitatively analyzing changes in the structure and/or the temporal changes of the oral cavity.

In addition, though the above issue about the enlargement factor has been described on an assumption that the tooth row is present along the 3D referential tomographic plane SS, it is almost certain that such an assumption is not true. In effect, it is mostly correct that patients' tooth rows are shifted entirely or partially from the 3D referential tomographic plane SS. Thus the imaging should consider this fact.

The conventional panoramic images are produced with no consideration of the issues due to changes in the foregoing enlargement factor and shifts of tooth rows from the 3D referential tomographic plane SS. Thus, it is very difficult to quantitatively analyze the structure from the conventional panoramic images. In this regard, it is desired to provide a panoramic imaging apparatus capable of imaging objects with accuracy even when tooth rows are different in shapes and/or positions every object, and/or regardless of what part of the same object' tooth row is imaged.

With consideration this, the panoramic imaging apparatus according to the present embodiment has a feature that image distortion due to differences in the enlargement factor even for the same tooth row can be removed, part by part, and it is possible to automatically and accurately identify a three-dimensional spatial real position (including a shape) of a patient' tooth row. Thus it is possible to provide three-dimensional panoramic images with higher identification accuracy of positions (shapes), than has been provided in the past.

In the present embodiment, a tomosynthesis technique (simply called tomosynthesis) is used to obtain images of tomographic planes or sections of an object. Practically, of frame data (sets of pixel data) acquired at intervals by scanning, a plurality of frame data relating to individual positions of a trajectory of the 3D referential tomographic plane obtained by projecting the 3D referential tomographic plane to the X-Y plane are selected. Such selected frame data are shifted to be overlapped with each other depending on their positions and added with each other (shift & add). Hence, an "optimal focus" referred to in the present embodiment means that "being best focused, being less defocused", which also means that a region of interest in an image is higher in resolution than other regions thereof or an entire image has a higher degree of resolution.

When a referential panoramic image is produced, data composing this image are stored in the image memory 54 and also displayed by the monitor 60 in an appropriate display mode. The display mode is decided by an operator's intention which is given through the operation device 58.

(Image Processing)

Figure 5:
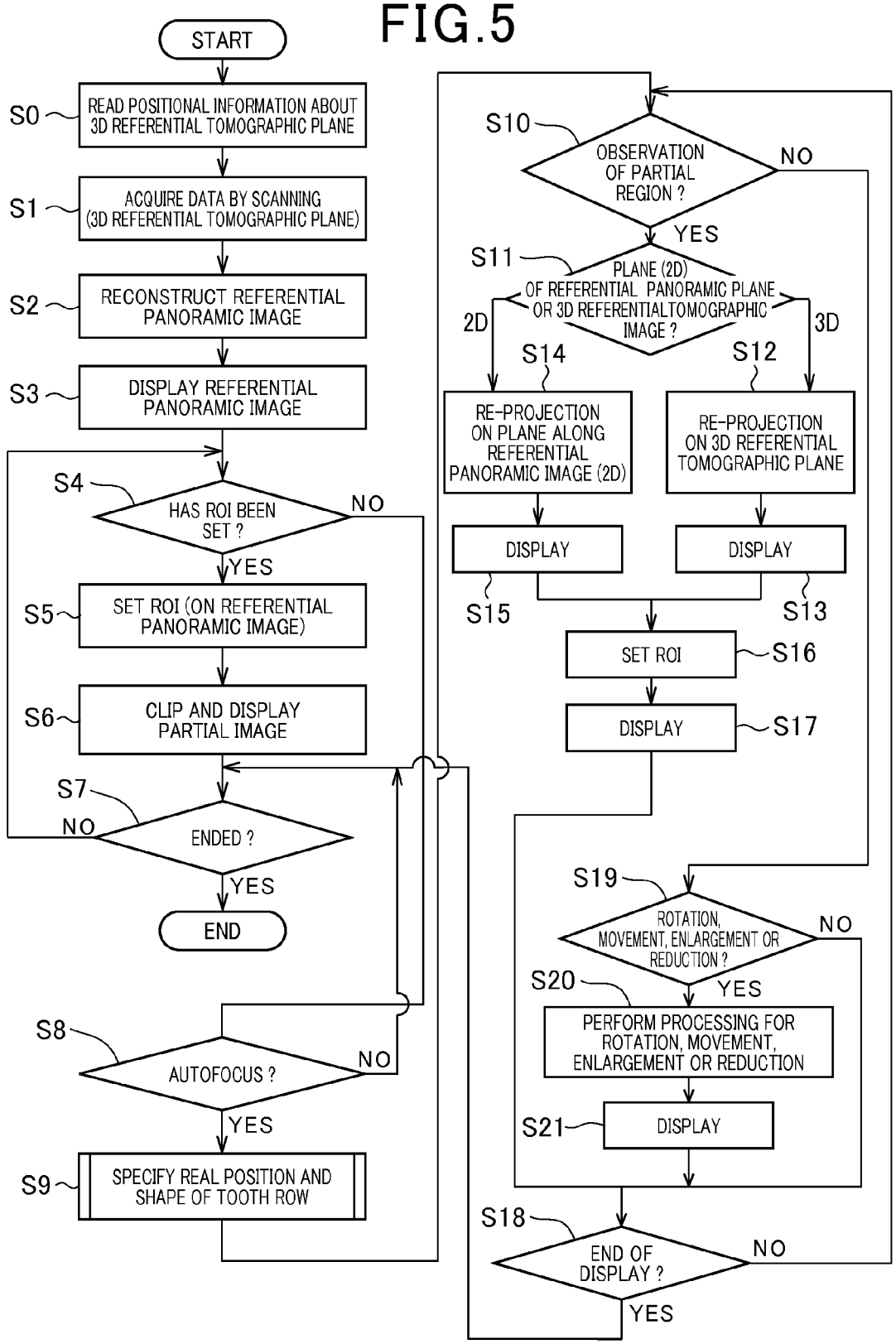
FIG. 5 is a flowchart showing an outline of processing for imaging performed cooperatively by a controller and an image processor provided in the panoramic imaging apparatus.

Referring to FIG. 5, processing performed cooperatively by the controller 57 and the image processor 56 will now be described. This processing includes, as described before, data acquisition by scanning, reconstruction of a referential panoramic image which is a pre-process, and production of 3D autofocus image (surface image) which is a main process, and display and/or measurement based on various modes which use the 3D autofocus images.

<Data Acquisition and Reconstruction of Referential Panoramic Image>

First, the controller 57 reads positional information of a 3D referential tomographic plane SS from the ROM 61 (step S0), after preparations such as positioning an object P for the imaging. This 3D referential tomographic plane SS may be a section decided in a statistical manner or a section previously set for each object.

The controller 57 then responds to an operator's command given through the operation device 58 to command scanning for acquiring data (Step S1). By this command, the rotary drive mechanism 30A, the movement mechanism 30B, and the high-voltage generator 41 start to be driven according to a predetermined control sequence. As a result, during rotation of the pair of the X-ray tube 31 and the detector 32 around the jaw of the object P, the X-ray tube 31 radiates a pulsed (or continuous wave) X-ray at intervals (or continuously). As described before, the pair of the X-ray tube 31 and the detector 32 is driven to rotate under a given drive condition so as to optimally focus on the 3D referential tomographic plane SS (refer to FIG. 6). The X-rays radiated from the X-ray tube 31 are transmitted through the object P to be detected by the detector 32. Accordingly, the detector 32 outputs, for example, at a rate of 300 fps, digital-quantity frame data (i.e., pixel data) in which amounts of X-ray transmission are reflected. The outputted frame data are temporarily stored in the buffer memory 53.

After the command for the scanning, the next command for the processing is provided to the image processor 56. The image processor 56 reconstructs a referential panoramic image PIst based on the shift & add process based on the tomosynthesis technique according to the spatial positions of the 3D referential tomographic plane SS, and the respective pixel values of the reconstructed image are stored (step S2). In this reconstruction process, the reconstructed image is multiplied by coefficients such that, similarly to the conventional situation longitudinal and lateral enlargement factors at the center of the anterior teeth become equal to each other.

Figure 7:
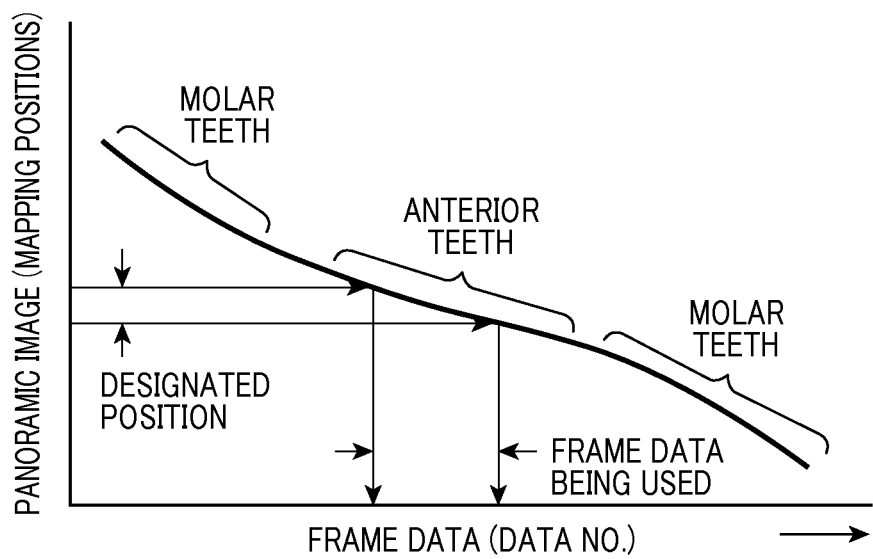
FIG. 7 is a graph explaining a relationship between frame data and mapping positions of the frame data to produce a panoramic image.

Although how to reconstruct an image is known, this will now be described a little. A set of frame data used for the reconstruction is obtained from a mapping characteristic which shows, as shown in FIG. 7 for example, mapping positions in the lateral direction of a panoramic image and a set of frame data which will be subjected to mutual addition for producing an image at the mapping positions. A curve showing this mapping characteristic consists of two curved portions which are steeper depending on molar teeth on both sides in the frame data direction (abscissa axis) and a curbed portion which is gentler than those of the two curved portions for the molar teeth depending on the anterior teeth. As shown, in this projection characteristic is used to designate a desired mapping position in the lateral direction of the panoramic image. Based on this designation, the set of frame data used to produce an image at the designated mapping position and amounts of shift (i.e. degrees of overlapping necessary frame data, which is a gradient of the curve) are designated. The designated frame data (i.e, pixel values) are shifted in accordance with the designated shift amounts to be overlapped on one another and added to each other, thus providing data of a longitudinally extending image at the designated mapping position. By repeating the designation of mapping positions and shift & add calculation through the entire range in the lateral direction of the panoramic image, it is possible to reconstruct the referential panoramic image PIst which focuses on the 3D referential tomographic plane SS.

Figure 8:
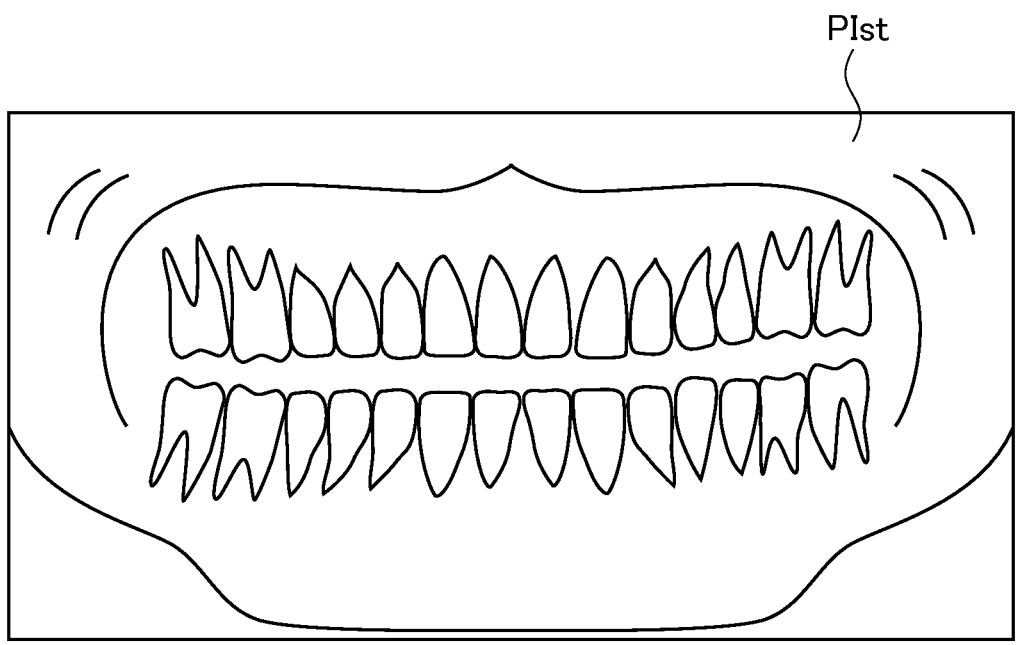
FIG. 8 is a view pictorially showing an example of a reference panoramic image.

The image processor 56 then displays the constructed referential panoramic image PIst on the monitor 60 (step S3), of which example is pictorially shown in FIG. 8

Since the referential panoramic image PIst is an image produced by shifting the frame data to be overlapped on one another and mutually adding them, this image is two-dimensionally rectangular. Longitudinal and lateral distortion at the anterior teeth in this image PIst, which is due to a difference of the enlargement factor in the longitudinal and lateral direction, is improved to some extent similarly to the conventional, because the image is multiplied by the coefficients so as to make the longitudinal and lateral enlargement factors equal to each other at the center of the anterior teeth. However, as advancing to and through the molar teeth, the longitudinal and lateral ratios of teeth become shifted from the correct ones. That is, the molar teeth are depicted to be less in size than the real size thereof. In many conventional cases, doctors are obliged to tolerate such panoramic images with distortion.

<Setting ROI on Referential Panoramic Image>

Then, the image processor 56 determines whether or not the operator uses the operation device 58 to set a ROI (a region of interest) on the referential panoramic image PIst (step S4). For example, the ROI shows a rectangular partial region in which the interpreter has a special interest. The ROI is not always limited to rectangular. In addition, the ROI can be set on the panoramic image automatically focused, which will be described later.

Figure 9:
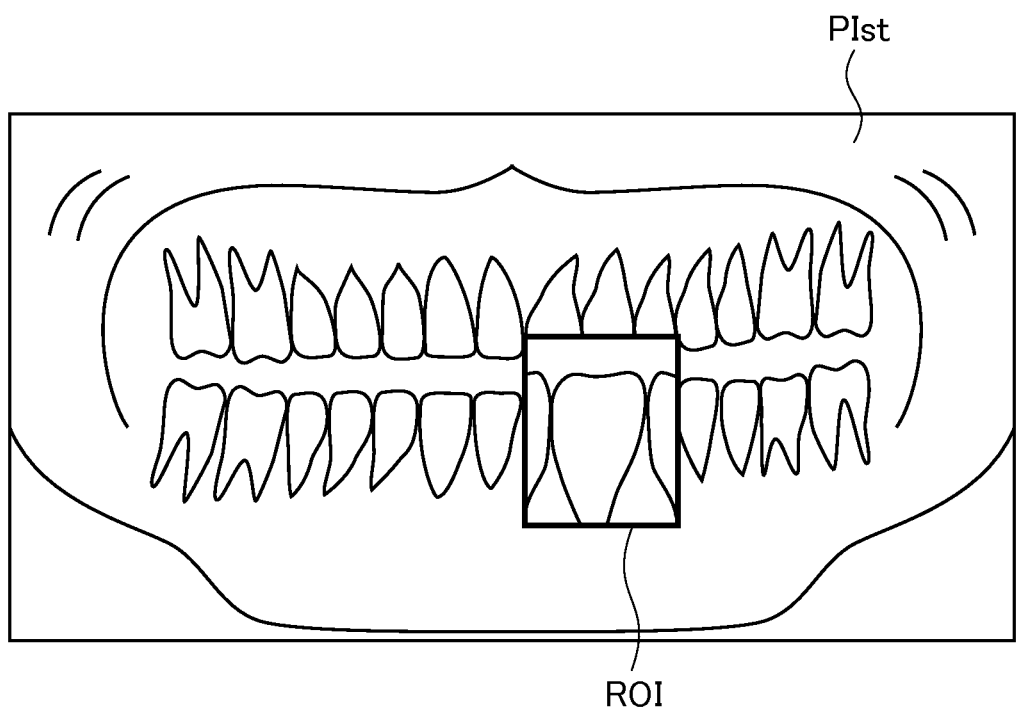
FIG. 9 is a view pictorially showing an example of the reference panoramic image on which a ROI is set.

When the determination at step S4 is YES, the image processor 56 responds to operational information from the operator to set the ROI on the referential panoramic image PIst (step S5). Then a partial image, which corresponds to the partial region sectioned by the ROI, is clipped out, and the partial image is displayed in a magnifying scale for example (step S6). For example, as shown in FIG. 9, this partial image is displayed in a superposed manner on the original referential panoramic image PIst. Alternatively, one or more partial images can be displayed by being mapped in a template in which blocks arranged to pictorially depict partial tooth rows in both the upper and lower teeth are arranged in a predetermined order.

Then the image processor 56 determines whether or not the processing should be ended. This determination depends whether or not there is operational information from the operator (step S7). When it is determined to continue the processing (NO at step S7), the processing is returned to step S4 for repetition of the foregoing steps. In contrast, when the determination shows completion of the processing, the processing shown in FIG. 5 is ended.

Meanwhile, when the determination at step S4 is NO, that is, when the ROI will not be set, the image processor 56 proceeds to the next step. Practically, it is determined based on operational information from the operator whether or not production of a 3D autofocus image is performed as a main process (step S8). If it is determined that this production will not be performed (NO at step S8), the processing is made to return to step S7 to determine ending the processing similarly as described.

<Specification of Position of Optimally Focused Section>

Figure 10:
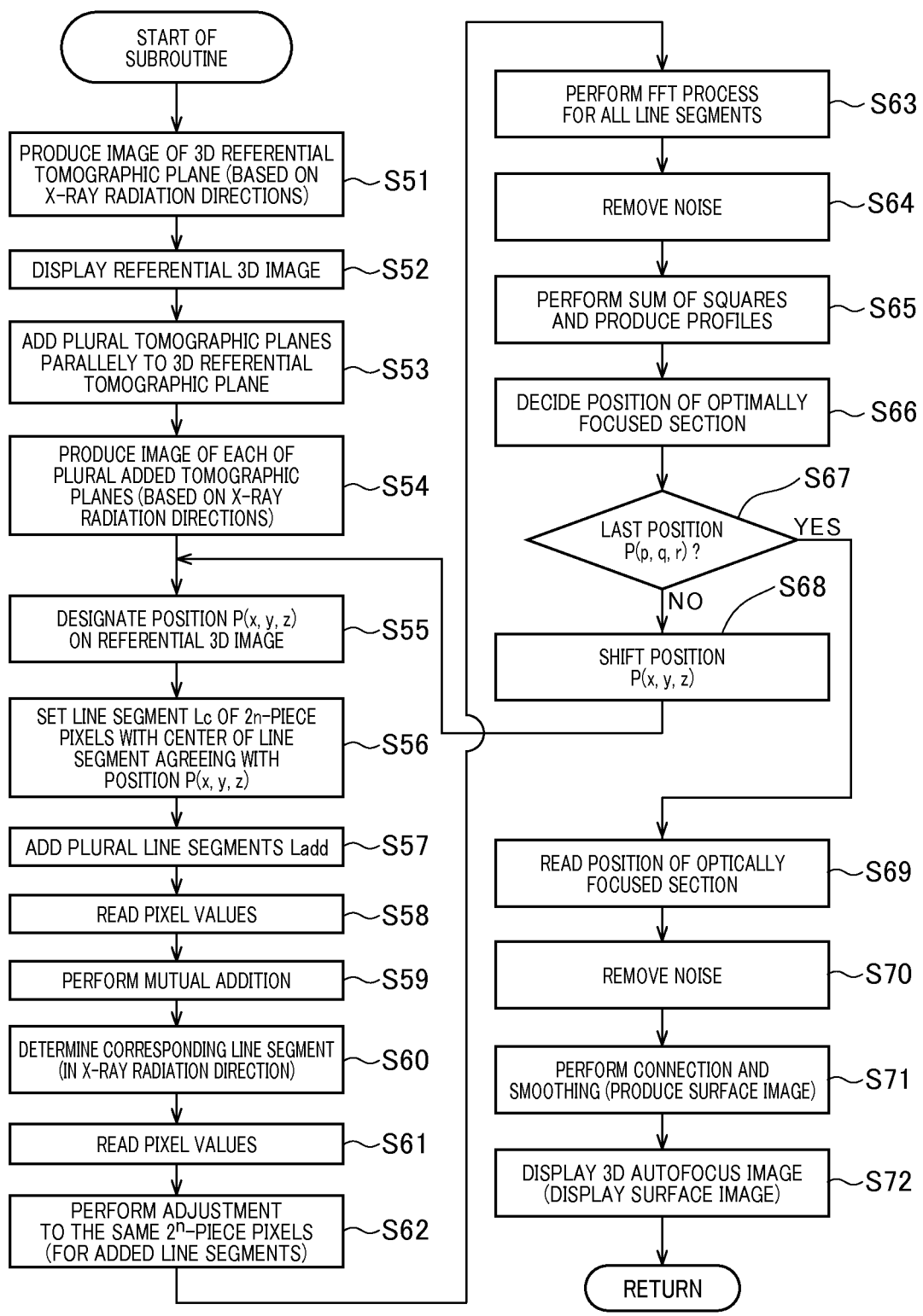
FIG. 10 is a flowchart outlining a process to identify the real positions and shapes of teeth, which is performed by an image processor.

In contrast, when it is determined that production of the 3D autofocus image is desired (YES at step S8), the processing proceeds to a subroutine provided at step S9. The processing executed at step S9 provides one of the features of the present invention, which is automatic identification of the real position and shape of a tooth row. In the identification, distortion in sizes of teeth is corrected, which distortion is due to the X-ray radiation directions oblique to the Z-axis direction FIG. 10 shows processing of the subroutine for such identification.

First, the image processor 56 considers the X-ray radiation directions to produce an image along the 3D referential tomographic plane SS (Step S51). Concretely the referential panoramic image PIst (rectangular) is coordinate-converted to a curved plane parallel with the 3D referential tomographic plane SS (a curved plane) to produce a 3D referential image along the coordinate-converted curved plane. Each of the pixels of the this 3D referential image is projected to the 3D referential tomographic plane SS along each of the X-ray radiation directions DRx by obtaining frame data by calculating changes of tomographic planes and coordinate-converting the obtained frame data. This provides a projection image along the curved 3D referential tomographic plane SS. The pixel values of this projection image are stored in the image memory 54.

Figure 11:
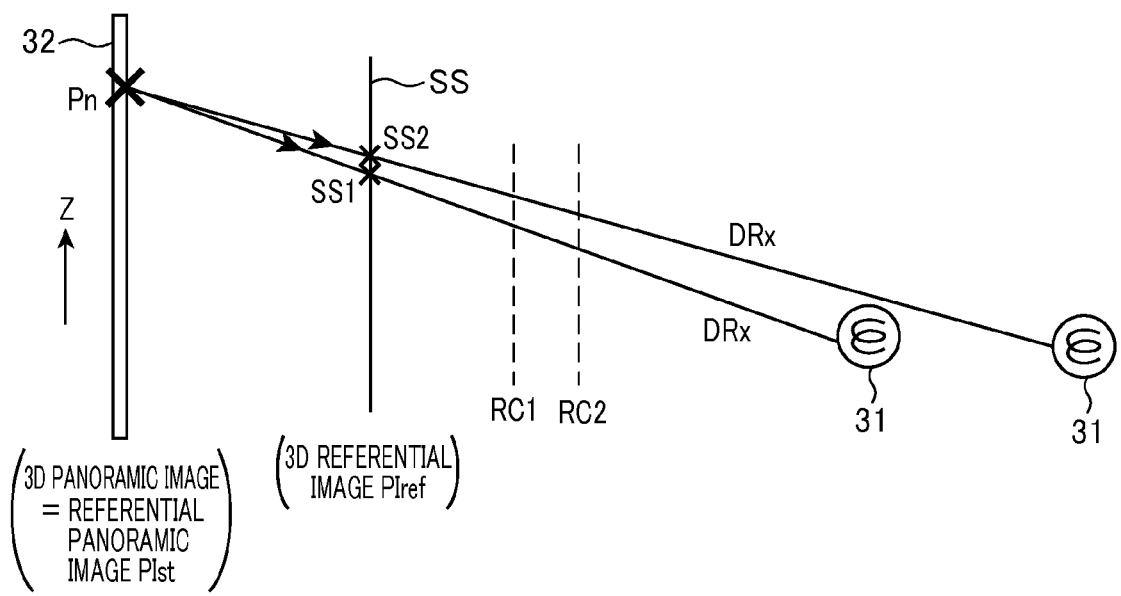
FIG. 11 is a view explaining a difference between angles from the same position in the Z-axis direction on a 3D panoramic image to the X-ray tube, which angles are caused by positional changes in the rotation center of the pair of the X-ray tube and the detector.

The projection is performed, as shown in FIG. 11, along each of the oblique projection directions directed to the rotation center RC (RC1, RC2), that is, the position where the X-ray tube 31 is present. When referring to the example in FIG. 11, a pixel located at a position Pn in the height direction (the Z-axis direction) of the 3D panoramic image will be projected to different positions SS1 and SS2 on the image of the 3D referential tomographic image SS, which is due to differences of positions at each of which the X-ray tube 31 is located.

The projection image produced by this projection is called a 3D referential image PIref in the present embodiment. This 3D referential image PIref is produced by oblique projection with consideration of characteristics of the foregoing enlargement factor, in which the oblique projection is performed at each of the pixels of the referential panoramic image PIst. By this oblique projection, enlargement of teeth belonging to the anterior teeth, which have large enlargement factors, is corrected to have real sizes thereof, while enlargement of teeth belonging to the molar teeth on both sides of the tooth row, which have small enlargement factors, is also corrected to have real sizes thereof. Hence, in the 3D referential image PIref, the teeth are depicted with their real sizes and have no or less distortion which is due to the size of the enlargement factors caused by the moved rotation center RC during the scanning. However it should be noted that this 3D referential image PIref is produced on the assumption that the tooth row is present at and along the 3D referential tomographic plane SS. It is rare that actual teeth are present at and along the plane SS, so that it is required to perform further processing to identify the real spatial positions and shapes of the teeth.

Figure 12:
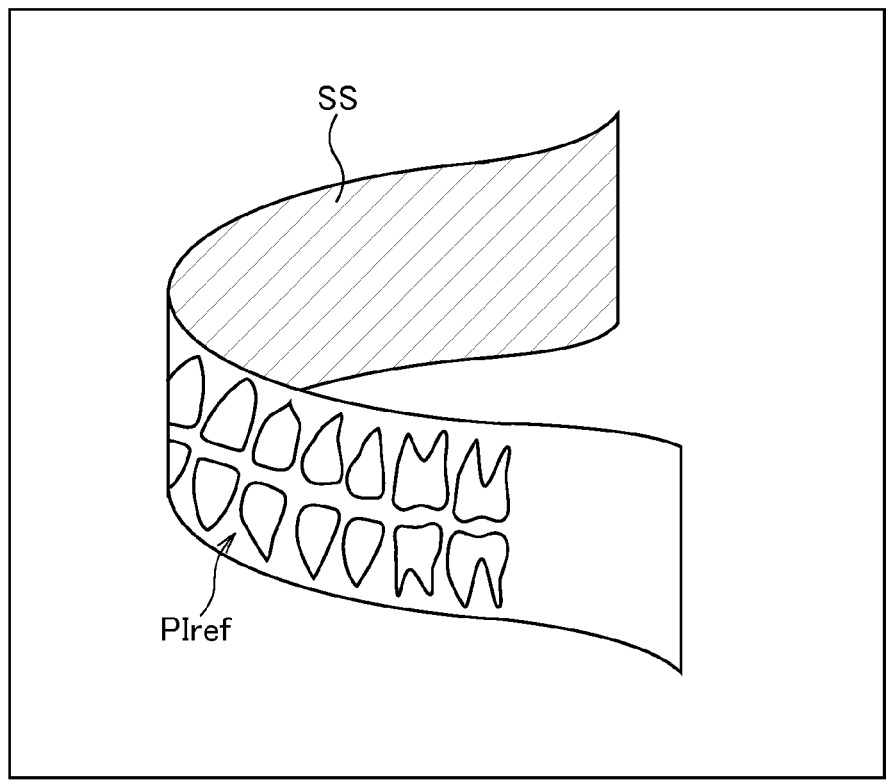
FIG. 12 is a view pictorially showing an example of a 3D reference image.

The image processor 56 displays the 3D referential image PIref on the monitor for operator's reference (step S52). This is shown in FIG. 12.

Figure 13:
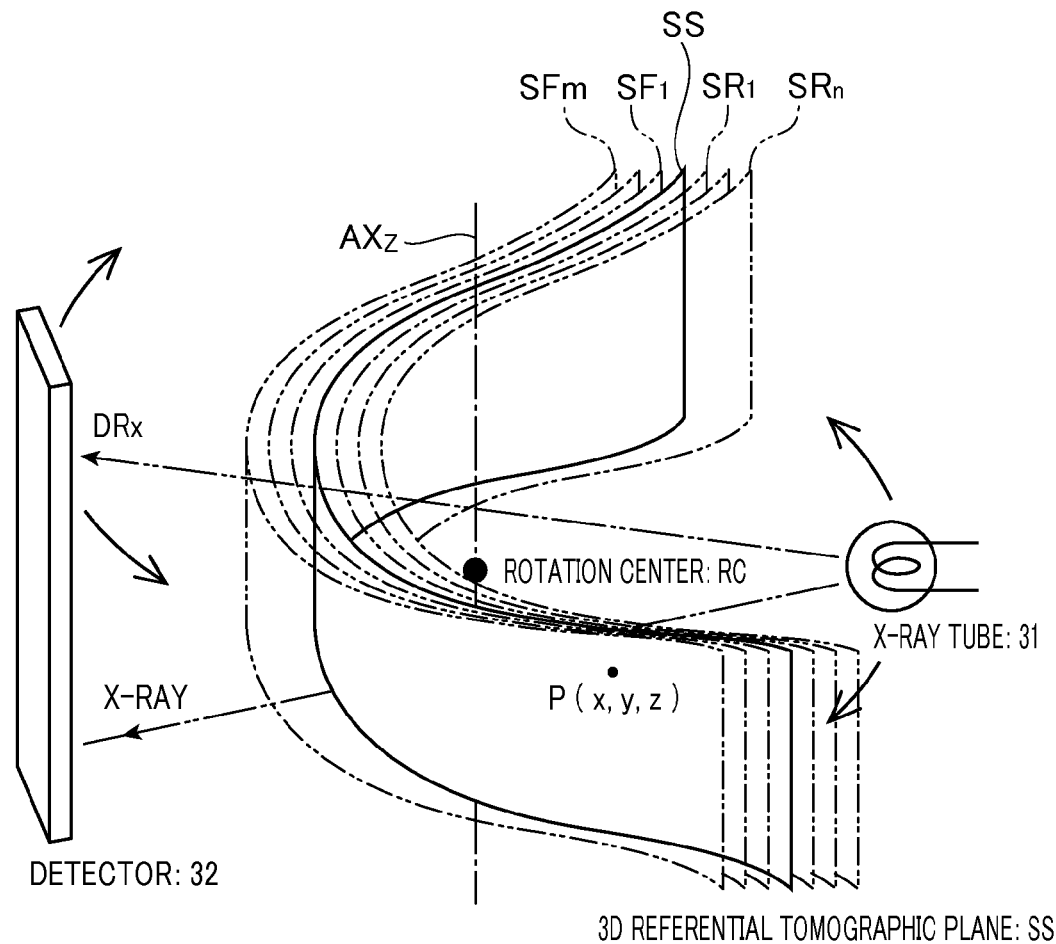
FIG. 13 is a perspective view explaining a plurality of parallel tomographic planes added to a 3D referential tomographic plane.
Figure 14:
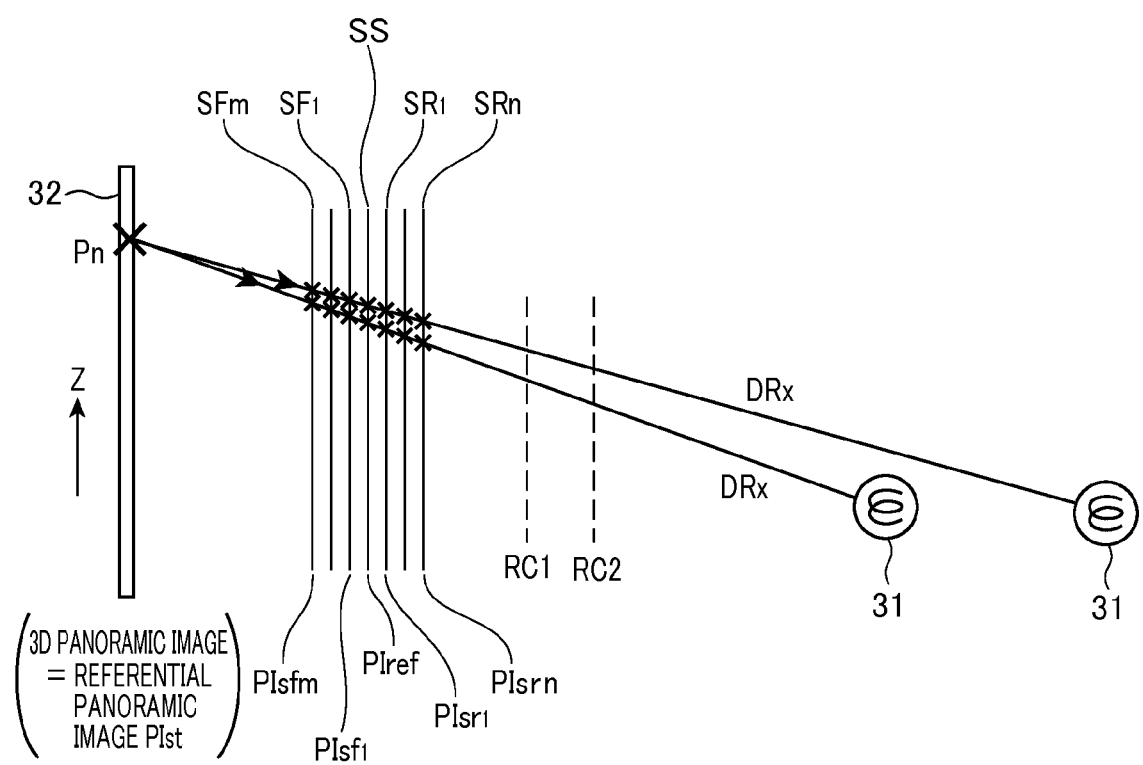
FIG. 14 is a view explaining differences of positions projected on the plurality of tomographic planes, which positions are obtained when the same Z-axial position on a 3D panoramic image is projected to the X-ray tube, wherein the positional differences are caused by positional changes in the rotation center of the pair of the X-ray tube and the detector.

The image processor 56 then adds a plurality of curved and parallel tomographic planes to the 3D referential tomographic plane SS (step S53). This is shown in FIG. 13. As shown, a plurality of tomographic planes are added to the 3D referential tomographic plane SS such that such tomographic planes are set before and after the plane SS respectively in the X-ray radiation directions DRx (i.e., the depth direction of the tooth row). By way of example, plural tomographic planes SFm-SF1 are located on the front side of the 3D referential tomographic plane SS at intervals of D1 (for example, 0.5 mm), while plural tomographic planes SR1-SRn are located on the rear side of the plane SS at intervals of D2 (for example, 0.5 mm). The intervals D1 and D2 may be equal to each other or different from each other. In addition, the number of tomographic planes to be added may be one on the front and rear sides of the plane SS respectively (i.e., m, n=1) or may be one or plural on either the front side or the rear side of the plane SS.

Incidentally, position data indicative of the virtually added tomographic planes SFm-SF1 and SR1-SRn are previously stored in the ROM 61 together with positional data of the 3D referential tomographic plane SS, so that the image processor 56 can perform the addition through reading of the positional data and loading them into a work area of the image processor 56. The heights of the tomographic planes SFm-SF1, SS, and SR1-SRn are decided appropriately in consideration of the maximum gradient of the X-ray radiation directions DRx and the height of the tooth row. Every time the identification processing is performed, the positions (the intervals D1, D2) of the tomographic planes to be added and the number thereof may be changed interactively.

Then, similarly to the process at step S51, with consideration of the angles of the X-ray radiation directions DRx, the image processor 56 projects the referential panoramic image PIst onto each of the tomographic planes SFm-SF1 and SR1-SRn by obtaining frame data through calculation of changes of tomographic planes and coordinate-changing the obtained frame data (step S54). As a result, images projected to the respective added tomographic planes SFm-SF1 and SR1-SRn are produced. The pixel values of such projection images are stored in the image memory 54.

In the present embodiment, the produced projection images are referred to as 3D added images PIsfm, . . . , PIsf1, PIsr1, . . . , PIsrn. Each of these 3D added images PIsfm, . . . , PIsf1, PIsr1, . . . , PIsrn is also produced by the oblique projections performed through the individual pixel positions of the referential panoramic image PIst, in which the oblique projections take into account of the foregoing differences in the enlargement factors. This is exemplified in FIG. 14, in which the same pixel existing at a position Pn in the height direction of a 3D panoramic image (i.e., the Z-axis direction) is projected onto different positions on the respective 3D added images PIsfm, . . . , PIsf1, PIsr1, . . . , PIsrn, which are due to differences in positions where the X-ray tube 31 is located.

Hence, the teeth depicted in the 3D added images PIsfm, . . . , PIsf1, PIsr1, . . . , PIsrn are depicted with their real sizes and distortion due to the variation of the enlargement factors, which is due to the movement of the rotation center RC during the scanning, is removed or suppressed from such 3D added images. It should be noted however that the 3D added images PIsfm, . . . , PIsf1, PIsr1, . . . , PIsrn are produced on the assumption that the tooth row is present at and along each of the 3D added images PIsfm, . . . , PIsf1, PIsr1, . . . , PIsrn.

As a modification, the plural 3D added images PIsfm, . . . , PIsf1, PIsr1, . . . , PIsrn thus produced can be displayed on the monitor 60 as three-dimensional images as they are or displayed on the monitor 60 as rectangular two-dimensional images produced through coordinate conversion.

Figure 15:
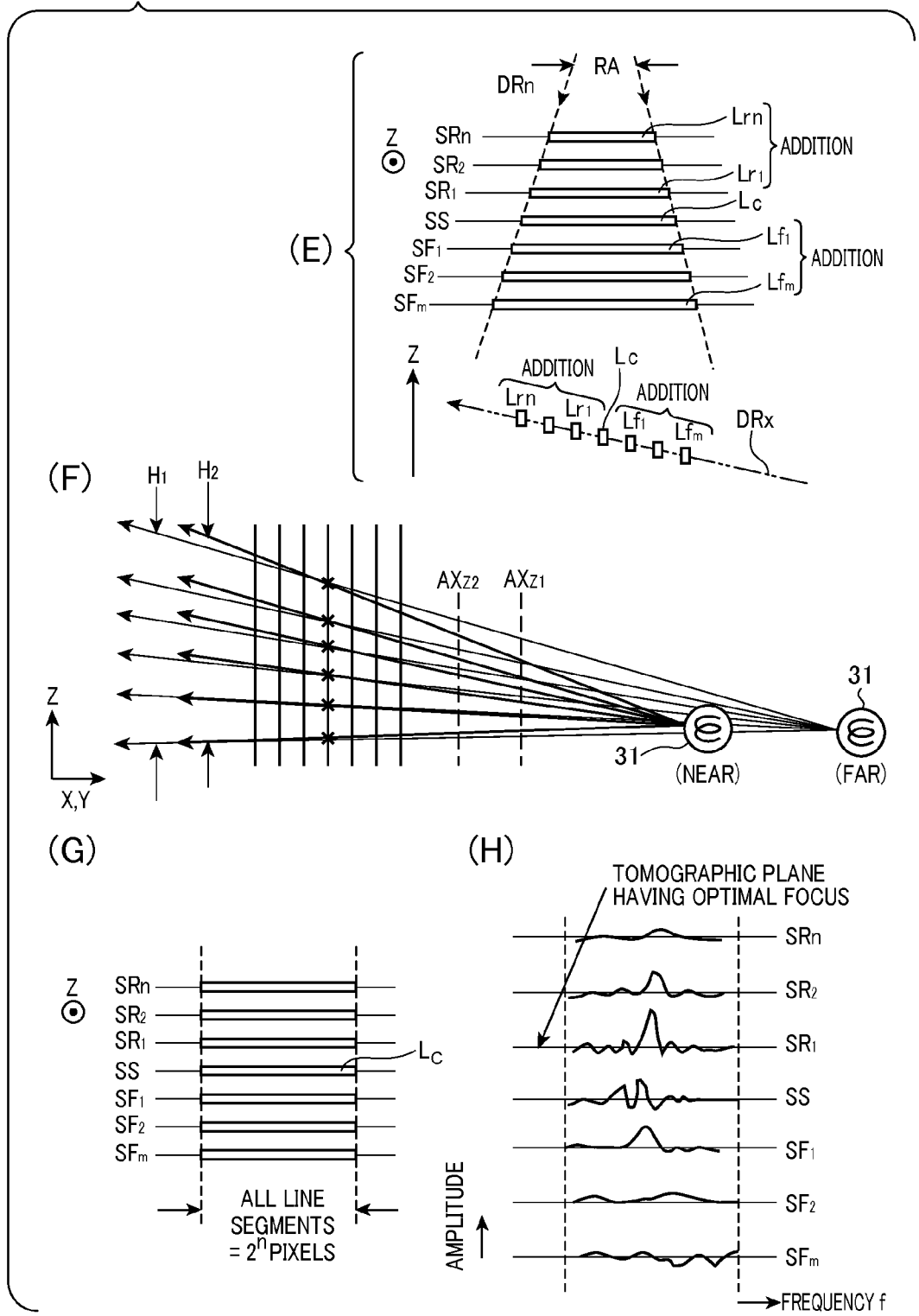
FIG. 15(1) is a view explaining, together with FIG. 15(2), the process to identify optimally-focused tomographic planes for each of positions on the 3D reference image.

The image processor 56 then designates an initial position P(x, y, z) on the 3D referential image PIref, that is, the 3D referential tomographic plane SS (step S55; refer to FIG. 15(A)). After this, the image processor designates a line segment Lc of a given length centering the designated position P(x, y, z) on the 3D referential image PIref (step S56; refer to FIG. 15 (B)). This line segment Lc has the given length corresponding to 2n pieces (n=1, 2, 3, . . . ; for example 128 pieces). As modifications, the line segment Lc can be drawn along a part of the curved 3D referential tomographic plane SS so that the line segment is curved or can be drawn in a limited range regarded as being linear.

Then the image processor 56 virtually adds plural line segments Ladd on the upper and lower sides of the designated line segment Lc(x, y, z) on the image, respectively, in which the plural line segments Ladd have the same length as that of the line segment Lc(x, y, z) (step S57; refer to FIG. 15(C)).

The image processor 56 then reads, from the image memory 54, the pixel values Pij of respective 2n-piece pixels composing each of the foregoing line segment Lc and plural line segments Ladd, and assigns the read pixel values to the respective line segments (step S58). The pixel values Pij have been already acquired and stored through the foregoing steps S51 and S54.

The image processor 56 then mutually add the pixel values Pij of the pixels corresponding to the line segment Lc and line segments Ladd to obtain 2n-piece pixel values Pij* that composes the line segment Lc(x, y, z), the 2n-piece pixel values Pij* being for a frequency analysis (step S59; refer to FIG. 15(D)). This addition makes it possible to reduce statistical noise in a later-described frequency analysis of changes in the pixel values, even if the pixel values of the line segment L(x, y, z) originally contain the statistical noise.

Then, on each of the 3D added images PIsfm, . . . , PIsf1 and PIsr1, . . . , PIsrn, the image processor 56 calculates the spatial positions of the line segments Lfm-Lf1 and Lr1-Lrn that face the line segment Lc(x, y, z) designated currently on the foregoing 3D referential image PIref, in the X-ray radiation direction DRx passing through the currently designated position P(x, y, z) (step S60; refer to FIG. 15 (E)). In this case, the current center position P(x, y, z) and the length of the line segment Lc, and the rotational positions of the X-ray tube 31 during the scanning are known. Hence, it is possible to calculate an X-ray radiation range RA which is fan-shaped when being viewed in the Z-axis direction, in which this range RA is formed by connecting each of both ends of the line segment Lc to the X-ray tube 31. As a result, as long as the position P(x, y, z) is designated, the spatial positions of the line segments Lfm, . . . , Lf1 and Lr1, . . . , Lrn limited by the X-ray radiation range in compliance with the designated position can also be designated by the image processor.

The process of step S60 to designate the position the position P(x, y, z) on the 3D referential image PIref is repeated until the same process for all the positions thereon is completed. Hence, in terms of effective X-ray radiation, the X-rays radiated from the X-ray tube 31 whose position comes near and farer transmit through the virtually set tomographic planes SFm-SF1, SS, and SR1-SRn within a range of H1 to H2 (a Z-axial range) in the fan shape (refer to FIG. 15 (F)). With consideration this fact, the tomographic planes SFm-SF1, SS and SR1-SRn themselves may be horseshoe-shaped sections having heights which change in every scanning direction and being parallel with each other.

When the line segments Lfm-Lf1 and Lr1-Lrn have been set as above, the image processor 56 reads pixel values Pij* of such line segments from the image memory 54 (step S61).

As shown in FIG. 15(E), since the X-ray tube 31 has a point X-ray source, the X-ray radiation range RA becomes a fan shape (when being viewed along the Z-axis direction). Hence, the pixels of each of the line segments Lfm-Lf1 and Lr1-Lrn are not $2^n$-pieces in number. Thus the image processor 56 multiplies each of the line segments Lfm-Lf1 and Lr1-Lrn by a coefficient depending on the distances D1 and D2 (refer to FIG. 6) in such a manner that the number of pixels of each of the added line segments Lfm-Lf1 and Lr1-Lrn becomes equal to the number of pixels, $2^n$, of the referential line segment Lc(x, y, z). Accordingly, as pictorially shown in FIG. 15(G), all the line segments Lfm-Lf1, Lc and Lr1-Lrn are formed to be parallel with each other and to have the same number of pixels, $2^n$ (step S62).

After this, the image processor 56 applies a frequency analysis to changes in the values of pixels of each of all the line segments Lf1-Lfm, Lc, and Lr1-Lrn (step S63). Thus, as shown in FIG. 15(H), as to the line segments Lfm-Lf1, L and Lr1-Lrn, there are provided analyzed results consisting of an abscissa axis showing frequencies and a vertical axis showing Fourier coefficients (amplitudes).

In the present embodiment, the frequency analysis is performed using fast Fourier transformation, but wavelet transformation may be adopted as such frequency analysis. Moreover, instead of such frequency analysis, a sobel filter to calculate the first derivation for edge extraction can be used for the equivalent process to the above. In using this filter, the position of a tomographic plane which provides an edge with a maximum filtered value can be regarded as an optimally focused position.

Figure 16:
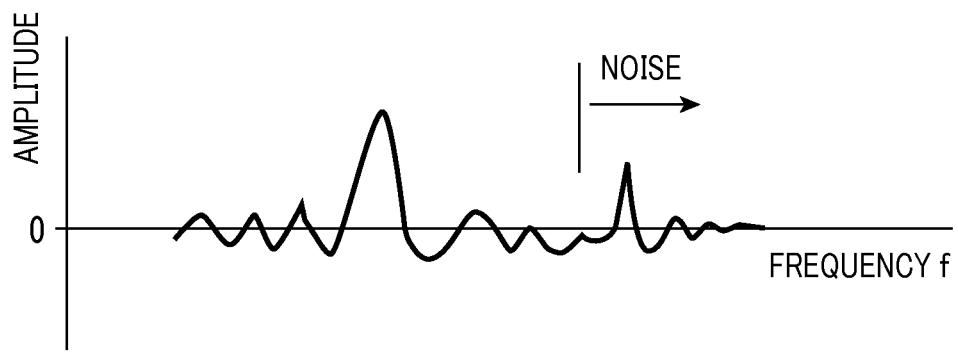
FIG. 16 is a graph exemplifying a frequency analysis result in an identification process for the optimally focused positions.
Figure 17:
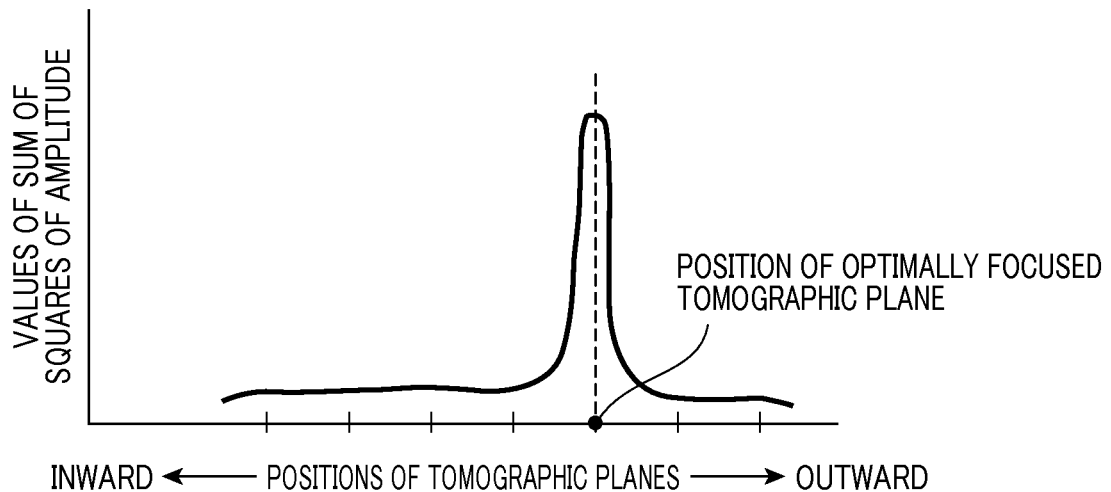
FIG. 17 is a graph exemplifying the position of an optimally focused tomographic plane obtained in the identification process for the optimally focused positions.

The image processor 56 then removes noise from the frequency analyzed results for all the line segments Lf1-Lfm, Lc, and Lr1-Lrn (step S64). FIG. 16 exemplifies the frequency analyzed characteristic for one line segment. Coefficients of frequency components which belong to a given frequency range next to a maximum frequency of the analysis are removed, with coefficients of the remaining high-frequency components adopted. The reason for such removal is that frequency components which are present in the given frequency range next to the maximum frequency provide noise signal components.

Further the image processor 56 calculates sums of squares for the coefficients of the frequency analyzed characteristic of each of the line segments, and produces a profile having a vertical axis to which the values of sums of squares are assigned and an abscissa axis to which the positions of the respective tomographic planes SFm-SF1, SS, and SR1-SRn are assigned, where the X-ray radiation direction DRx passing through the initial position P(x, y, z)=P(0, 0, 0) passes through the positions of such tomographic planes (step S65). This profile is exemplified in FIG. 17. In this profile, the positions of the tomographic planes mean the positions the plural tomographic planes SF1-SFm, SS, and FR1-FRn in the X-ray radiation direction DRx (i.e., the depth direction of the tooth row).

Figure 18:
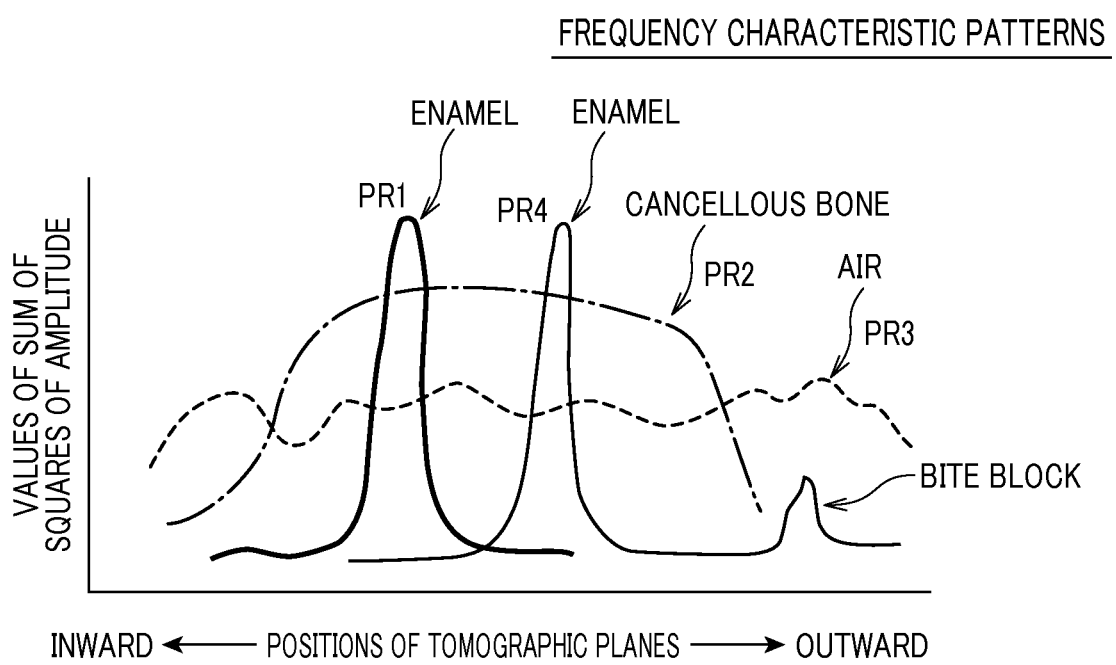
FIG. 18 is a graph exemplifying frequency characteristic patterns changing depending on tomographic plane positions.
Figure 19:
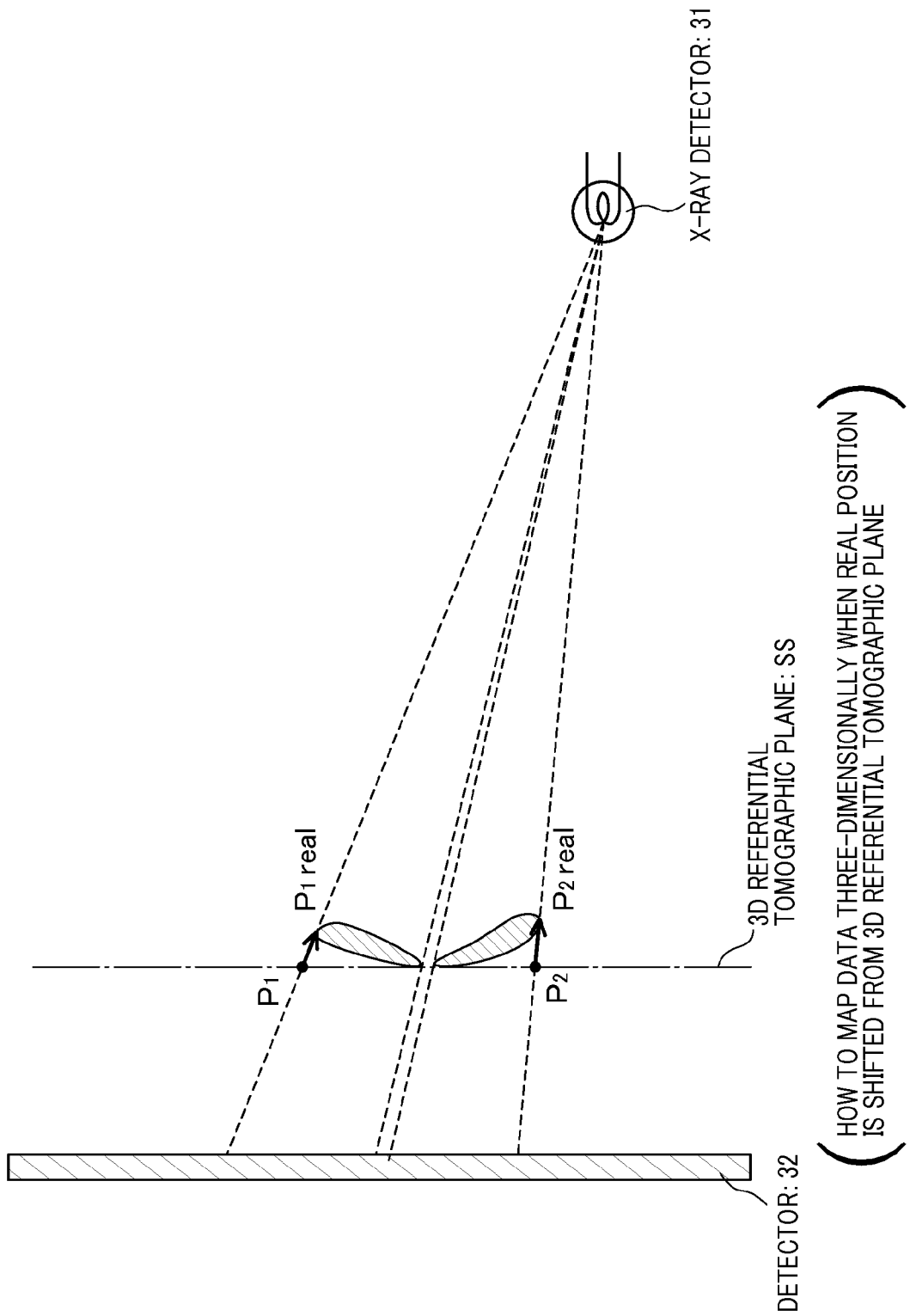
FIG. 19 is a view explaining a state where the real positions of teeth are deviated from the 3D referential tomographic plane.
Figure 20:
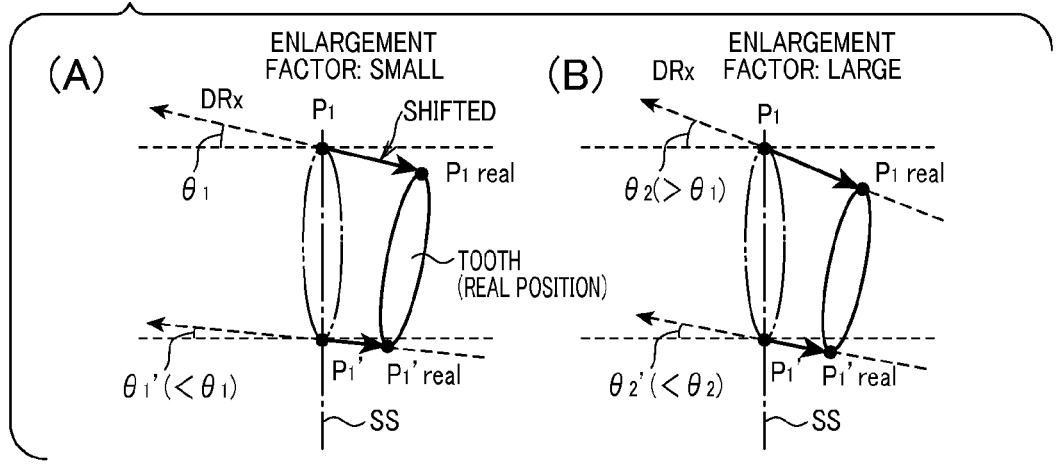
FIG. 20 is a view explaining a state where a tooth is shifted from the position of the 3D referential tomographic image to its real position depending on the size of an enlargement factor.
Figure 21:
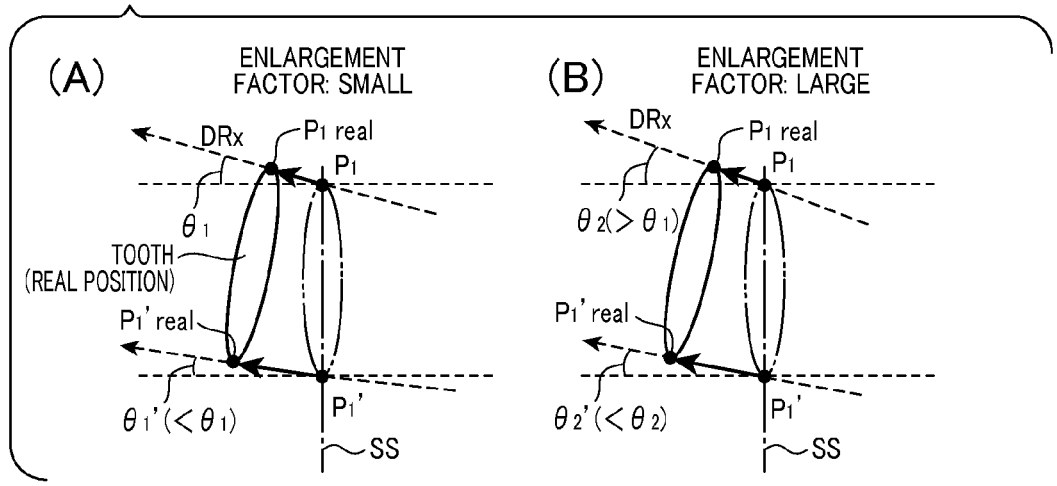
FIG. 21 is a view explaining a state where a tooth is shifted from the position of the 3D referential tomographic image to its real position depending on the size of an enlargement factor.

FIG. 18 exemplifies, as typical patterns, a plurality of types of profiles PR1, PR2, PR3 and PR4 respectively showing substances composed of enamel, cancellous bone, air and bite blocks. If there is a substance of enamel, i.e., tooth, anywhere in the X-ray radiation direction DRx that passes through the currently designated position P(x, y, z), the profile PR1 has a sharp peak. If there is cancellous bone in that X-ray radiation direction DRx, the profile PR2 has a gentle convex curve. Similarly, if there exists only air in that X-ray radiation direction DRx, the profile PR3 tends to show a curve having no specific peaks. Moreover, when the bite block is present in that X-ray radiation direction DRx, the profile PR4 exhibits two sharp peaks. Of such two peaks, one appearing inward (on the X-ray tube side) in the X-ray radiation direction DRx shows that the substance thereat is enamel, while the other appearing outward (on the detector side) shows that the substance thereat is the bite block. Data indicating the patterns of the profiles shown in FIG. 18 are previously stored, as reference profiles, in the ROM 61 in the form of a reference table.

Hence, the image processor 56 refers to the reference table to specify an optimum focused position of the tooth in the X-ray radiation direction DRx passing through the currently designated position P(x, y, z) (step S66).

That is, a pattern recognition technique is used to determine that the profile obtained in the last step S65 corresponds to which of the reference profiles PR1-PR4. First, when the obtained profile is the reference profile PR2 or PR4, such a profile is withdrawn from the consideration. In contrast, when the obtained profile corresponds to the reference profile PR1 (i.e., enamel), it is identified that the section position showing its peak, i.e., the position of any of the plural tomographic planes SF1-SFm, SS, FR1-FRn, is optimally focused. Moreover, when the obtained profile is fit to the reference profile PR4, it is also identified that an inward sectional position expressing a peak (a sectional position showing enamel on the X-ray tube side), in other words, the position of any of the plural tomographic planes SF1-SFm, SS, FR1-FRn, is optimally focused.

By the foregoing specifying steps, it is identified that a portion of the tooth depicted at the currently designated position P(x, y, z) is actually present at which position in the depth direction. In effect, a tooth portion depicted on the 3D referential image PIref along the 3D referential tomographic plane SS may be present on the front or rear sides of the plane SS. The real position of the tooth portion in the imaging space is specified precisely by the foregoing specifying steps. In other words, it can be understood that a tooth portion depicted on the 3D referential image PIref under the condition that the tooth portion is on and along the 3D referential tomographic plane SS is shifted to its real spatial position by the foregoing specifying steps.

Figure 22:
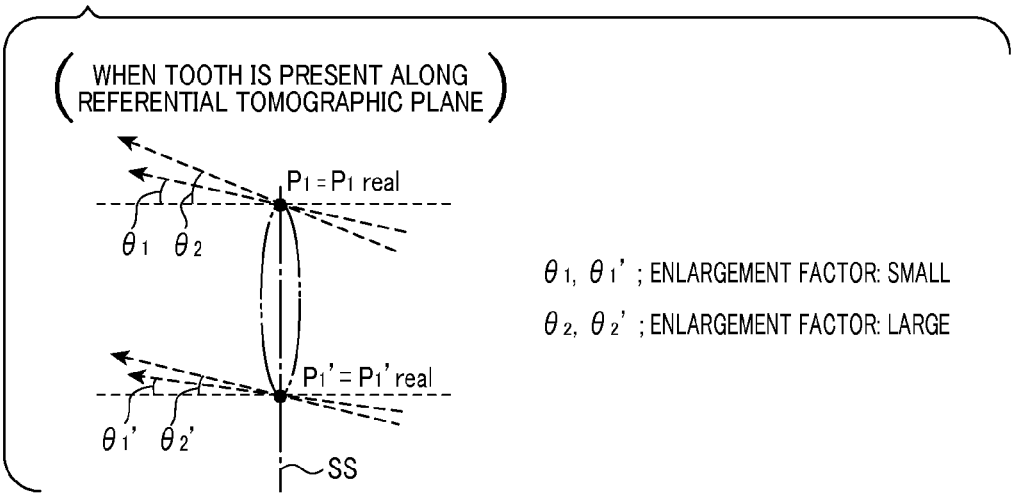
FIG. 22 is a view explaining a state where a tooth is shifted from the position of the 3D referential tomographic image to its real position depending on the size of an enlargement factor.

As a result, as shown in FIGS. 19-22, every time the position P(x, y, z) is designated, a position P1 on the 3D referential tomographic plane SS (i.e., in the 3D referential image PIref) is shifted to a position P1real (or a position P2 is shifted to a position P2real). In particular, the positions of the line segments Lfm-Lf1 and Lr1-Lrn which are set on the plural added tomographic planes SFm-SF1 and FR1-FRn are set in consideration of the oblique angle θ of each of the X-ray radiation directions DRx. Thus, the shifted position P1real in the case of a smaller oblique angle θ (such as $θ_1$, $θ_1'$: refer to FIGS. 20(A) and 21(A)) becomes lower in the Z-axis direction than in the case of a larger oblique angle θ (such as $θ_2$, $θ_2'$: refer to FIGS. 20(B) and 20(B)). Accordingly, the shifted position P1real can be compensated in distortion depending on the oblique X-ray radiation angle θ, i.e., the size of the enlargement factor. Incidentally as shown in FIG. 22, when the tooth is present at and along the 3D referential tomographic plane SS, a relationship of P1=P1real is met. In this case, the 3D referential tomographic plane SS, at and along which it is assumed that the tooth is present, provides a real position, thus providing a shift amount of zero.

The image processor 56 then proceeds to step S66, at which data indicating the real position of the tooth portion is stored every position P(x, y, z) in the work area thereof.

In this way, as to the currently designated position P(x, y, z) on the 3D referential image PIref (i.e., the 3D referential tomographic plane SS), practically, as to the first designed initial position P(0, 0, 0), a specifying process is performed in the depth direction passing through the initial position P(0, 0, 0). As the specifying process, filtering is performed to check whether or not there is a portion of the tooth (enamel). And when it is checked that there is such a tooth portion, an optimally focused position for the tooth part is specified in the depth direction.

Figure 23:
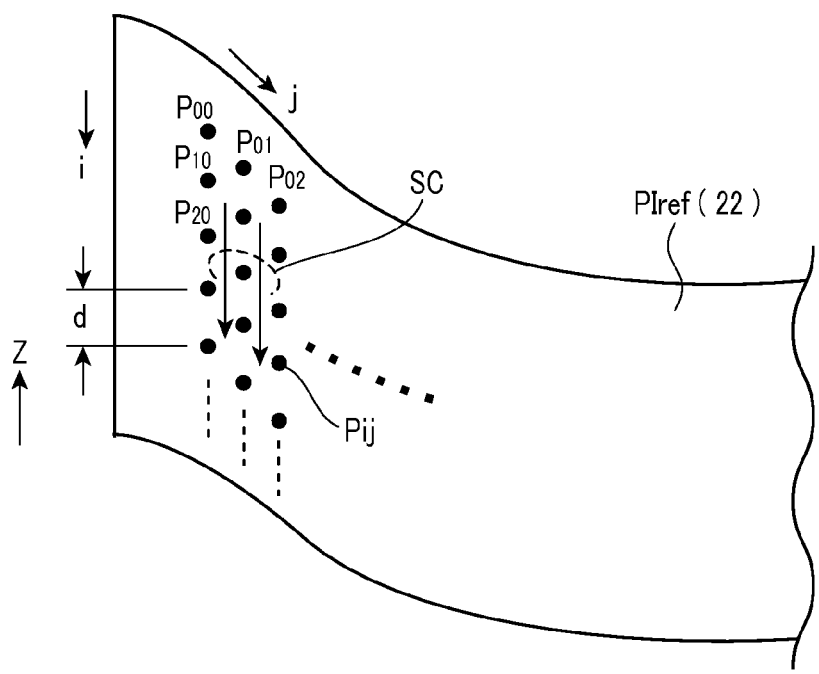
FIG. 23 is a perspective view explaining a process for moving processing points on the 3D reference image in order to perform the position identifying process.

After this, as shown in FIG. 23 for example, the image processor 56 determines whether or not the foregoing specifying steps have been completed at all determination points (sampling points) P previously set on the 3D referential image PIref (step S67). This determination is executed by checking whether or not the currently processed position P(x, y, z) is the last position P(p, q, r). If this determination is NO which shows the specifying steps have not been completed at all the determination points P, the image processor 56 shifts the determination point P(x, y, z) by one (step S68), before returning to the foregoing step S55 to repeat the foregoing series of specifying steps.

As shown in FIG. 23, the plural determination points P are previously mapped with given intervals on the 3D referential image PIref (i.e., the 3D referential tomographic plane SS). In the example shown here, along both the vertical direction i and the horizontal direction j of the 3D referential image PIref, the positions P are mapped at the same given intervals d in the vertical and horizontal directions. Alternatively, the internals d may be differentiated between the vertical and horizontal directions i and j from each other. The direction along which the shift is carried out at step S68 may be any of the vertical, horizontal and oblique directions on the 3D referential image PIref. As shown in FIG. 23, the shift can be made along the first vertical direction i, and the line is transferred in the horizontal direction j to repeat the shift in the second vertical direction i. This shifting manner is repeated regularly (refer to a reference numeral SC in the figure). Oppositely to this, the shift can be made along the horizontal direction j, and the line is transferred in the vertical direction i to repeat the shift in the horizontal direction. Moreover, the shift may be performed obliquely.

Meanwhile, when the foregoing specifying steps have completed for all the plural determination points P, the determination at step S67 reveals YES during the repeated processing. This means that, every determination point P, an optimally focused sectional position has been detected in the depth direction passing through the position P on the 3D referential tomographic plane SS (including determination whether or not there is an optimally focused position). In this case, the processing proceeds to a connection process of the optically focused sectional positions.

<Process to Connect Optimally Focused Sectional Positions>

Figure 24:
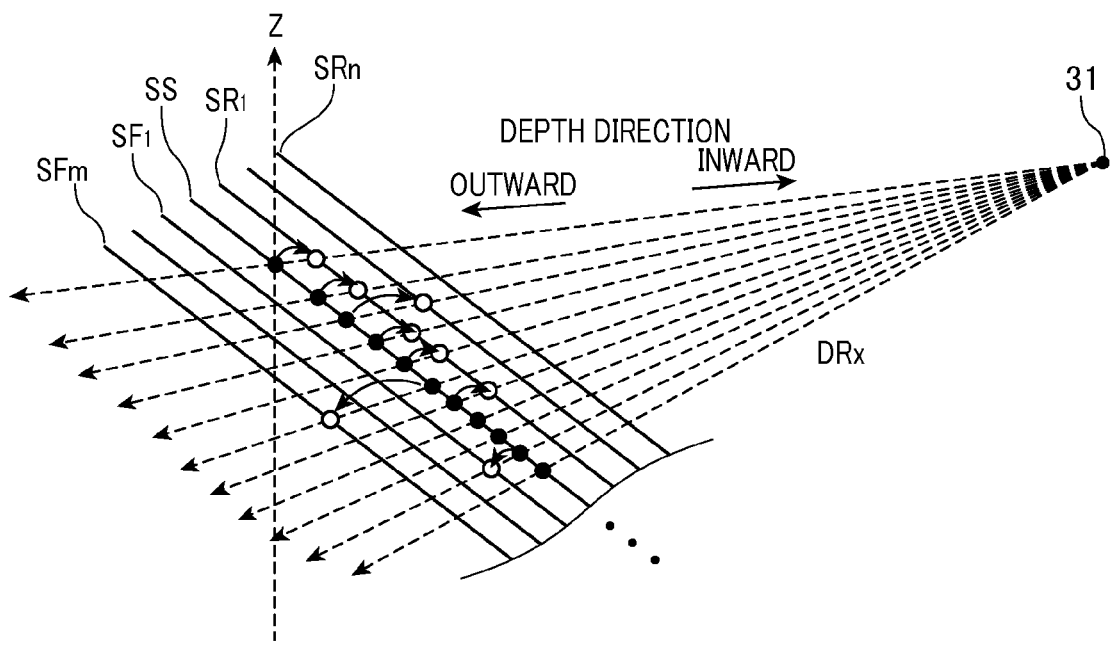
FIG. 24 is a perspective view explaining identification of the position of an optimally focused tomographic plane being identified every processing point and its abnormal identification.

When it is determined YES at the foregoing step S67, the image processor 56 reads data indicative of the optimally focused sectional positions specified and stored at step S66 (step S69). The data of these sectional positions show positions in each of the X-ray radiation directions DRx passing through each of the determination points P(x, y, z). This is pictorially exemplified in FIG. 24. In this drawing, filled circles indicate determination points P(x, y, z) on the 3D referential image PIref (i.e., the 3D referential tomographic plane SS). In this case, the vertical and horizontal directions of the curved 3D referential image PIref are denoted by (i, j). In FIG. 24, as shown by open circles, for example, an optimally focused sectional position at a determination point P(x00, y00, z00) for i, j=0, 0 is read as a position actually preset at the position of a tomographic plane SR1, which is shifted inwardly by one section (toward the X-ray tube side). An optimally focused sectional position at a determination point P(x01, y01, z01) for i, j=0, 1, which is next to the determination point for i, j=0, 0, is read as a position also actually present at the position of the tomographic plane SR2, which is shifted inwardly by one plane. Furthermore, an optimally focused sectional position at a determination point P(x02, y02, z02) for i, j=0, 2, which is next to the determination point for i, j=0, 1, is read as a position actually present at the position of a tomographic plane SR3, which is shifted inwardly by one plane further. In FIG. 24, for the sake of an easier understanding the process at step S68, only one position in the Z-axis direction (i.e., the vertical direction) are shown, but, at each of the positions in the Z-axis direction, the process at step S68 is performed.

The image processor 56 then performs removal of noise (step S70). In the example shown in FIG. 24, an optimally focused sectional position at a determination point P(x03, y03, z03) for i, j=0, 3 is read as a position actually present at the position of a tomographic plane SFm, which is shifted outwardly by no less than m-piece sections (toward the detector side). In such a case, the image processor 56 applies, for example, a threshold checking to a difference between the sectional positions to find out noise, thus regarding it abnormal data. Hence, the data of mutually adjacent sections are for example smoothed to smoothly connect the sections and replaced with a new set of smoothed positional data. Alternatively, data used for the data replacement may be produced by selectively giving priority to sectional data closer to the outside of the detector. As another alternative, instead of such compensation using the data replacement, abnormal data may simply be removed from data being processed. It is also possible that the abnormal data to be removed include data abnormal in the Z-axis direction.

The image processor 56 then connects the positions with noise removed (that is, the positions showing the enamel) and three-dimensionally smoothes the connected positional data, whereby a surface image tracing the enamel is produced (step S71). Furthermore, the image processor 56 displays the produced surface image, as a 3D autofocus image PIfocus which is a three-dimensional panoramic image all portions of which are automatically optimally focused, on the monitor 60 at a desired view angle (step S72).

Figure 25:
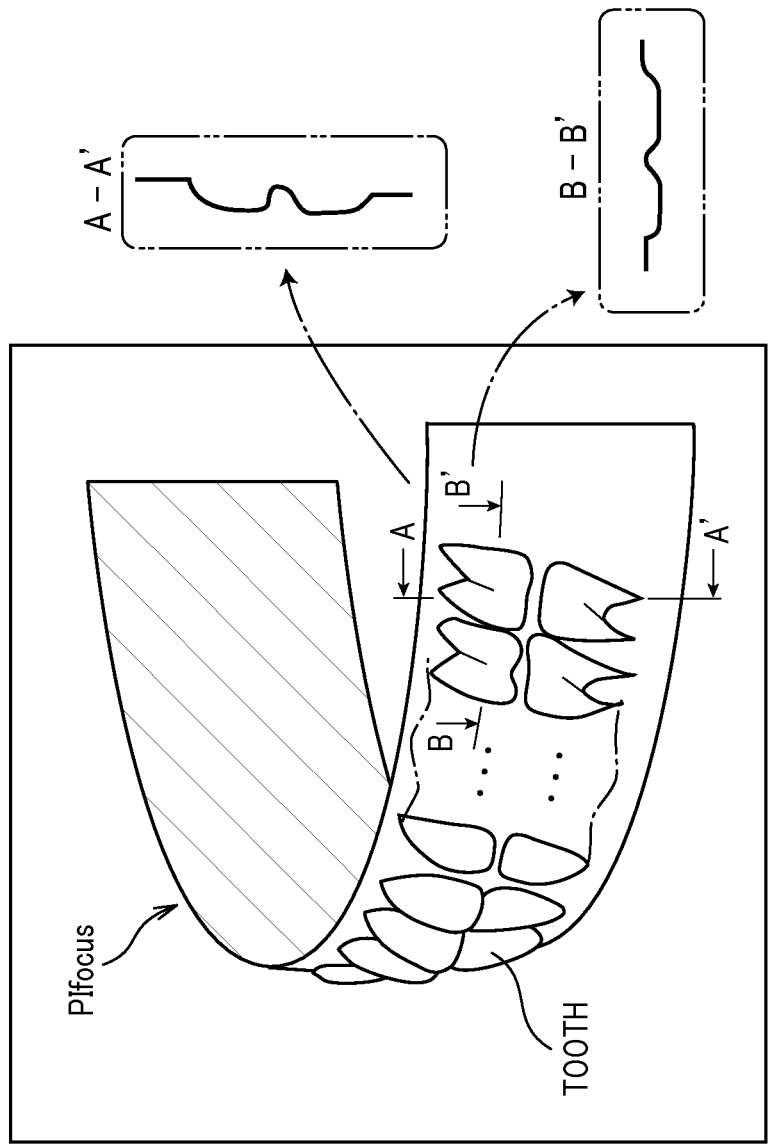
FIG. 25 is a view pictorially showing identification of the position of an optimally focused tomographic plane and a 3D autofocus image produced through smoothing.

Hence, as shown in FIG. 25, it is possible to provide the 3D autofocus image PIfocus at the desired view angle, where the 3D autofocus image structurally shows the tooth row of the oral cavity of the object P in the clearest manner. In the drawing, the curved horseshoe-shaped range S shows a range to display the 3D autofocus image PIfocus and solid lines show the real positions and shapes of the tooth row. As shown by an A-A' line and a B-B' line, portions such as part of the gum (alveolar bone), mandibular antra, the articulation of jaw, and the carotid artery can be depicted by a tomographic plane produced apart a given distance from the edges of the teeth (mainly the enamel) and the tomographic plane is projected three-dimensionally. In such a case, although it is not guaranteed that such portions other than the teeth are optimally focused, there will not be an unnatural feeling to the 3D panoramic images. Of course, the calculation for optimal focusing may be improved to optimally focus on such portions other than the teeth in the whole calculation, depending on purposes of diagnosis.

In this way, the produced 3D autofocus image PIfocus is entirely curved to trace the tooth row and its surface is rough. This "roughness" depicts the real position and shape (contour) of each of the teeth by densities of pixel values. The remaining parts can also be depicted with no unnatural feeling.

Hence, the autofocus image PIfocus indicating the real position and shape of the tooth row of each object P.

<Various Display Processes>

The image processor 56 then provides the operator with chances to observe the produced 3D autofocus image PIfocus in other modes. Practically, in response to operation information from the operator, the image processor 56 determines whether or not it is desired to display the 3D autofocus image PIfocus in other modes, in an interactive manner.

Figure 26:
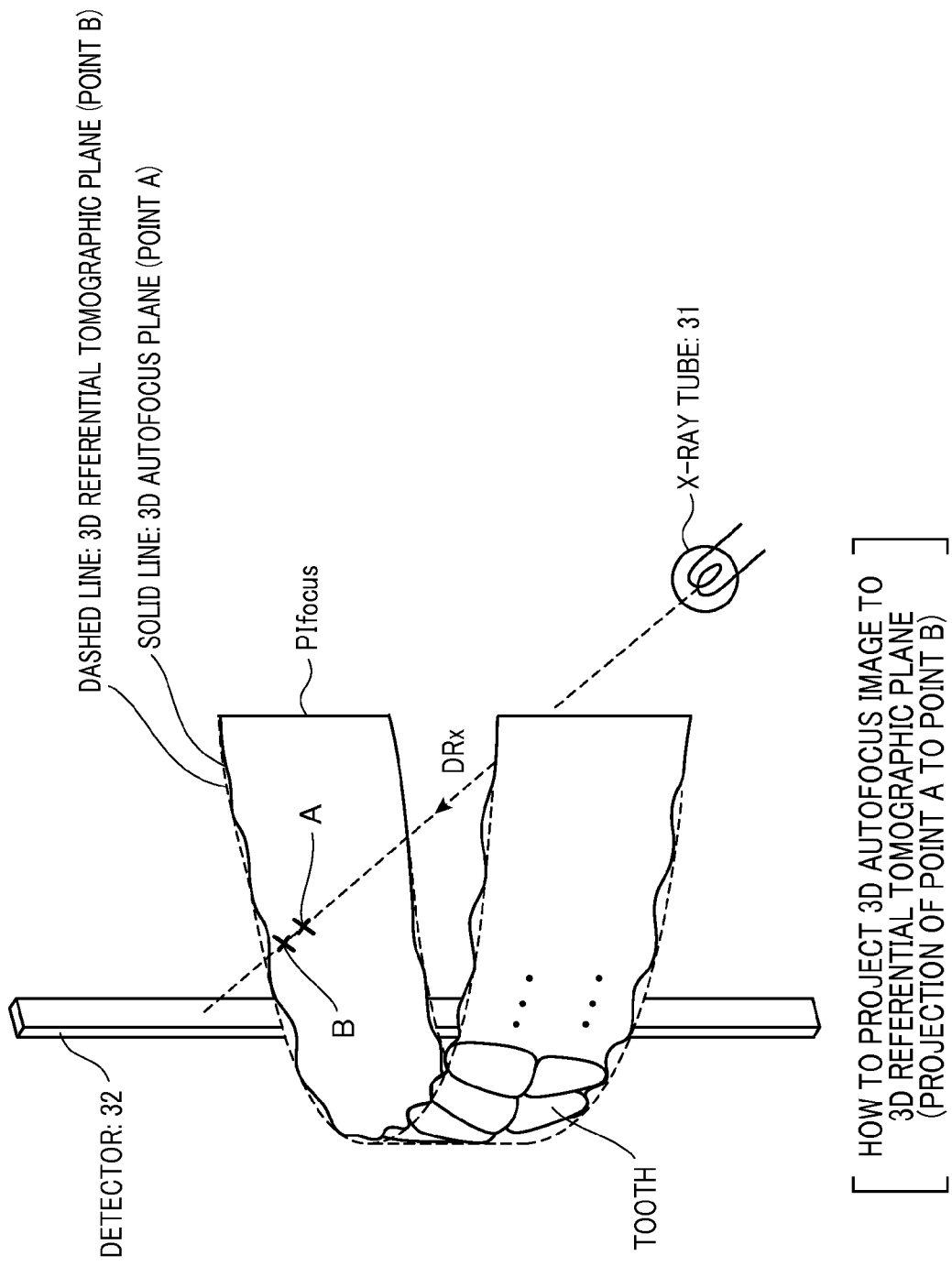
FIG. 26 is a view explaining a concept of processing for projecting the 3D autofocus image onto the 3D referential tomographic plane.

By way of example, the image processor 56 determines whether or not it is desired to observe a partial region of the 3D autofocus image (3D panoramic image) PIfocus (in FIG. 5, step S10). When the determination at this step S10 is YES, it is further determined based on information from the operator whether the partial region is desired to be observed using a 3D referential tomographic plane SS or the rectangular plane (two-dimensional) of a referential panoramic image (step S11). When it is determined at this step S11 that the 3D referential tomographic plane SS is used, the image processor 56 re-projects the 3D autofocus image PIfocus to the 3D referential tomographic plane SS in the X-ray radiation directions DRx passing through the pixels of the plane SS respectively (step S12). This re-projection is shown in FIG. 26. This re-transmission can be performed by a subpixel method, by which each pixel of the 3D referential tomographic plane is sectioned by subpixels corresponding to the three-dimensional pixels and then subjected to the re-projection.

A re-projected image to the 3D referential tomographic plane SS is displayed on the monitor 60 as a 3D reference image PIproj-3D (step S13). An example of this 3D reference image PIproj-3D is shown in FIG. 27.

Meanwhile, when it is determined at step S11 that the rectangular plane of the referential panoramic image PIst is desired, the image processor 56 re-projects the 3D autofocus image PIfocus to the rectangular plane, that is, the plane of a referential panoramic image (step S14). This re-projection is also performed by the known subpixel method, by which each pixel of the plane of the referential panoramic image is sectioned by subpixels corresponding to the three-dimensional pixels and then subjected to the re-projection. This re-projection is conceptually shown in FIG. 28. This re-projected image is displayed as a 2D reference image PIproj-2D on the monitor (step S15). An example of this 2D reference image PIproj-2D is shown in FIG. 29.

Figure 27:
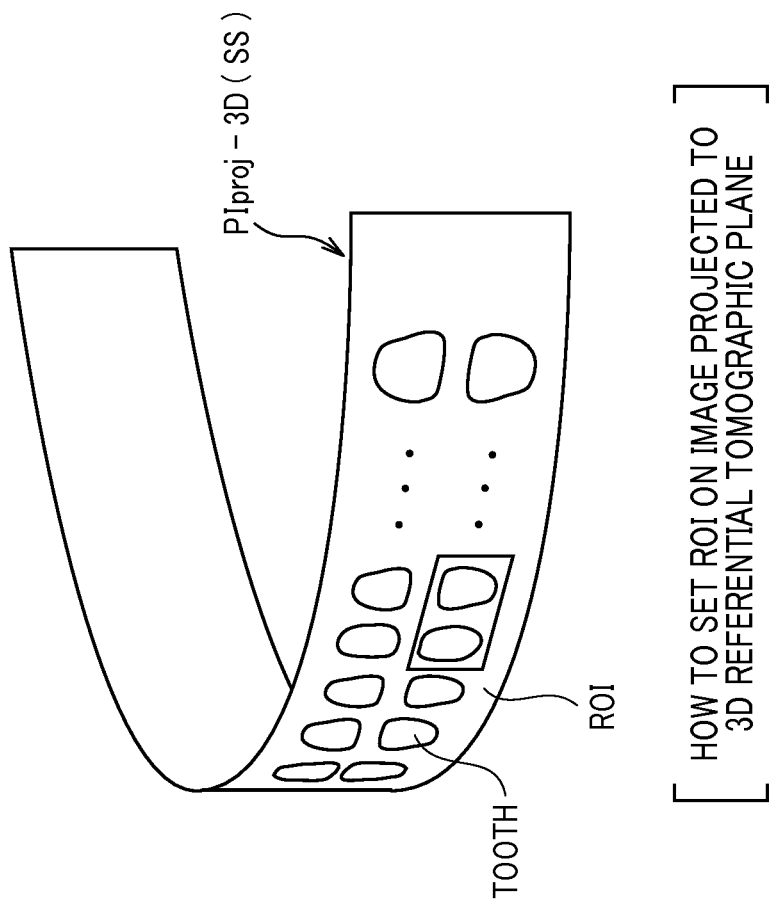
FIG. 27 is a pictorial view explaining an image projected to the 3D referential tomographic plane and a ROI set on the image.
Figure 28:
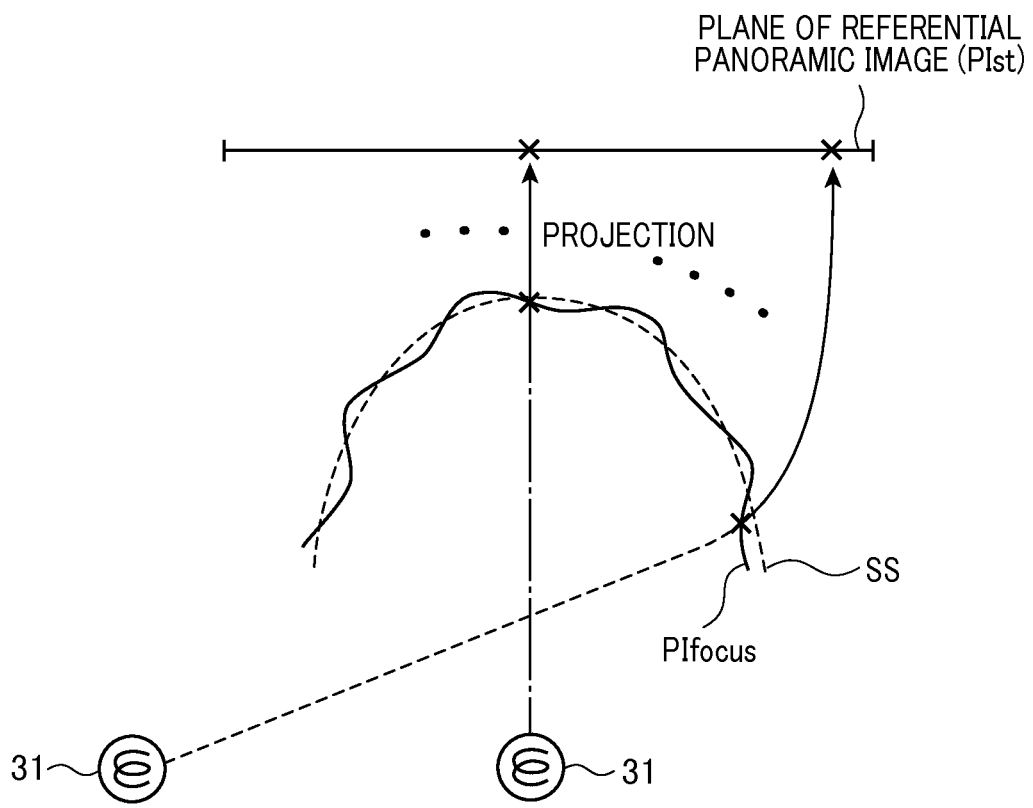
FIG. 28 is a view explaining a concept of processing for projecting the 3D autofocus image to a two-dimensional plane owned by a referential panoramic image.
Figure 29:
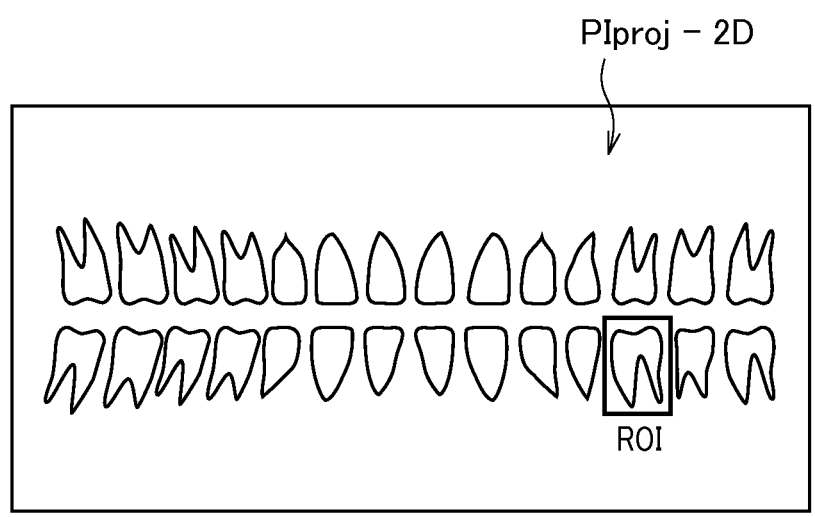
FIG. 29 is a view pictorially explaining a 2D reference image and a ROI which is placed thereon.

The operator sets a desired ROI (region of interest) of, for example, a rectangle on either the 3D reference image PIproj-3D or the 2D reference image PIproj-2D (step S16; refer to FIGS. 27 and 29). A partial region designated by this ROI is enlarged, and superposed on the currently displayed 3D reference image PIproj-3D or the 2D reference image PIproj-2D, for example (step S17). Of course, such a re-projected image may be displayed differently from the panoramic image, displayed together with the panoramic image in a divided manner, or displayed using a template consisting of a plurality of display blocks mapped along the tooth row.

The image processor 56 then determines whether or not the foregoing set of processes should be ended, using information from the operator (step S18). When being determined YES, the processing is returned to step S7, while being determined NO, the processing is returned to step S10 for repeating the foregoing processing.

By the way, when it is determined at step S10 that the partial region will not be observed, the image processor 56 further determines interactively whether or not the currently displayed 3D automatic image PIfocus is necessary to be rotated, moved, and/or enlarged or reduced for display (step S19). If this determination is YES, the image processor responds to a command to rotate, move, and/or enlarge or reduce the 3D autofocus image PIfocus, and displays such a processed image (steps S20, S21). Then the processing proceeds to step S81 for repeating the foregoing steps.

Of course, the display modes will not be limited to the foregoing, but can adopt various other modes such as color representation.

When the operator commands to end the foregoing processing, the image processor 56 ends the processing via performance at steps S18 and S7.

Incidentally, after setting at step S16, the processing may skip the display at step S17 to directly proceed to step S19. In such a case, the ROI which has been set may be displayed together with the rotated, moved, and/or enlarged or reduced image at step S21.

(Operation and Effects)

The panoramic imaging apparatus according to the preset embodiment provides the following distinguished operations and effects.

First, differently from panoramic images produced by the conventional panoramic imaging apparatus, there can be provided, as a 3D autofocus image PIfocus (a three-dimensional panoramic image), an image focusing on at least the entire region of the tooth row. According to this image, when the teeth are curved in the vertical direction, their real positions and shapes are optimally focused every points (i.e., sampling points) in the vertical direction. In addition, the processing for this optimal focusing is automatically performed in response to only an operator's intended command issued one time, so that the 3D autofocus image PIfocus is displayed. That is, the autofocus function is provided. Additionally to this, the resultant 3D autofocus image PIfocus can be rotated before being displayed and can be subjected to enlargement and display of a ROI region set thereon, thus providing many variations for image observation. Hence, it is easier for interpreters to very precisely examine the entire region of the tooth row, providing the examination with higher accuracy. It is almost never required to re-try the X-ray imaging, thus avoiding an amount of X-ray exposure from increasing, which is due to re-trying the imaging. The panoramic imaging apparatus according to the present embodiment is suitable for screening.

In addition to the above, changes in the enlargement factor, which are caused due to changes of the rotation position, i.e., due to changes of the rotation center RC of the pair of the X-ray tube 31 and the detector 32 during the scanning, are also corrected during the processing for producing the 3D autofocus image PIfocus. Hence, image distortion resulting from changes in the enlargement factor is also removed or suppressed, thus providing images which reflect therein real sizes and real shapes of the teeth.

In obtaining panoramic images by the conventional panoramic imaging apparatus, changes in the enlargement factor result in the enlargement factor changes between the molar teeth and the anterior teeth. This causes a reduction in the degree of accuracy of measurement and understanding of distances and lengths on the image. In contrast, in the present embodiment, such problems are resolved, and images or measurement information with accuracy and very real sizes can be provided, thus being fitted to detailed structural observation of the tooth row being imaged.

In particular, when the 3D autofocus image PIfocus is re-projected to the 3D referential tomographic plane or the two-dimensional rectangular plane of a referential panoramic image as stated, the positional correspondence to the three-dimensional autofocus image can be obtained, although a re-projected image involves a certain amount of distortion. Hence, for example, distances such as vertical lengths of teeth can be measured accurately.

Moreover, in the panoramic imaging apparatus of the present invention, the three-dimensional positions of the X-ray tube 31 and the detector 32, which are moved during the data acquisition (scanning), are previously known. This means that it is not necessary to previously measure information indicative of distances of tomographic planes (sections) in the imaging space by using a phantom, which is seen in the conventional case. From this point of view, operators' operability is improved and calculation load of the image processor 56 is alleviated.

In consequence, there can be provided three-dimensional panoramic images in which the entire region of the tooth row is optimally focused, the actual states (positions and shapes) of the tooth row are three-dimensionally depicted with higher precision, and distortion of the image which is due to differences in the enlargement factor is removed as much as possible.

(Variations)

The foregoing embodiment has described the example that provides optimally focused three-dimensional images of the tooth row of oral cavity of an object. This example can be developed into various other modes. By way of example, there is the use of a marker (or X-ray marker). The marker, which is made of radiation-absorbing material having an appropriate X-ray absorption factor, is arranged in the oral cavity. In this arranged state, like the foregoing embodiment, data are acquired to positionally recognize the marker and focusing and imaging a section including the marker.

FIG. 30(A) exemplifies a marker. As shown, a clip 70 has two square chips 71 serving as markers and a wire member 72 with a spring mechanism connects and holds the two chips 71 such that the chips are opposed to be located alternately. The chips 71 are made of a material whose X-ray absorption factor is higher than that of the oral cavity, whereby the chips can function as markers to the X-ray.

Figure 30:
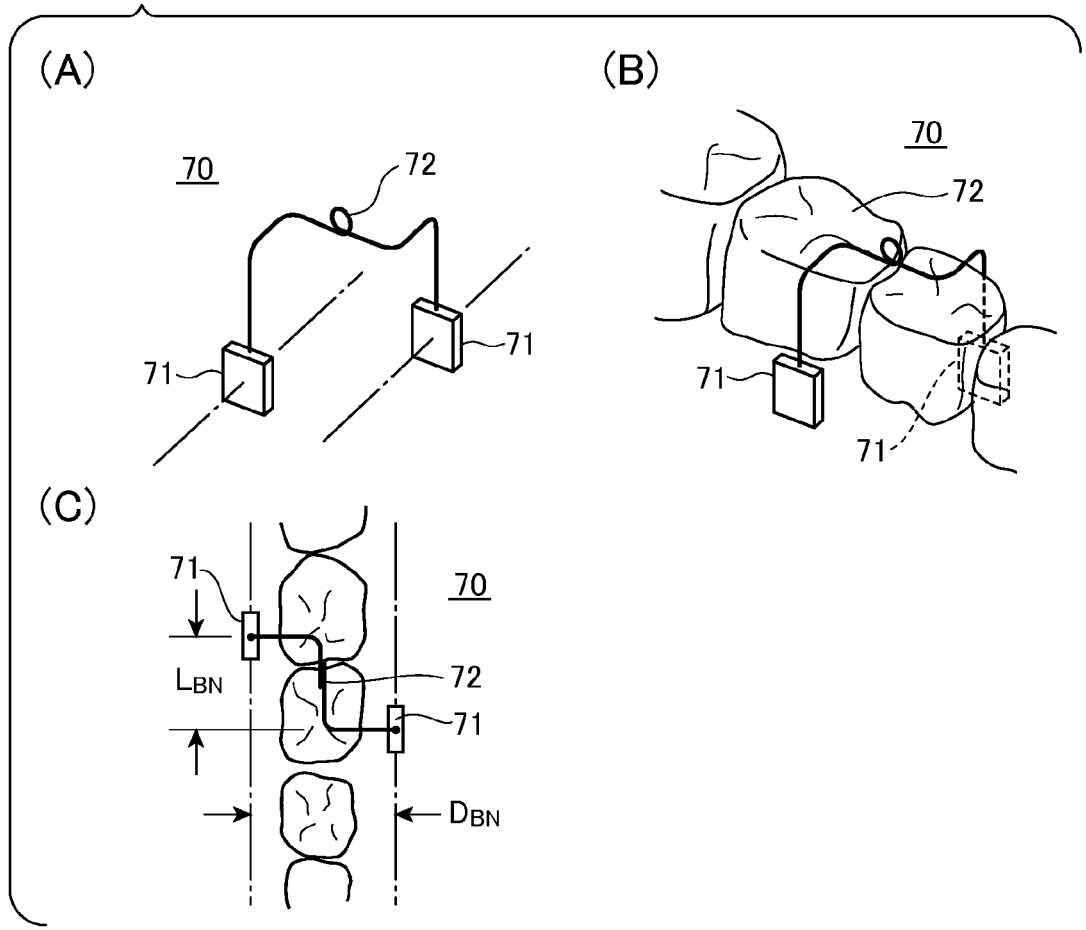
FIG. 30 is a view explaining a marker and how to use the marker, which is described by a modification.
Figure 31:
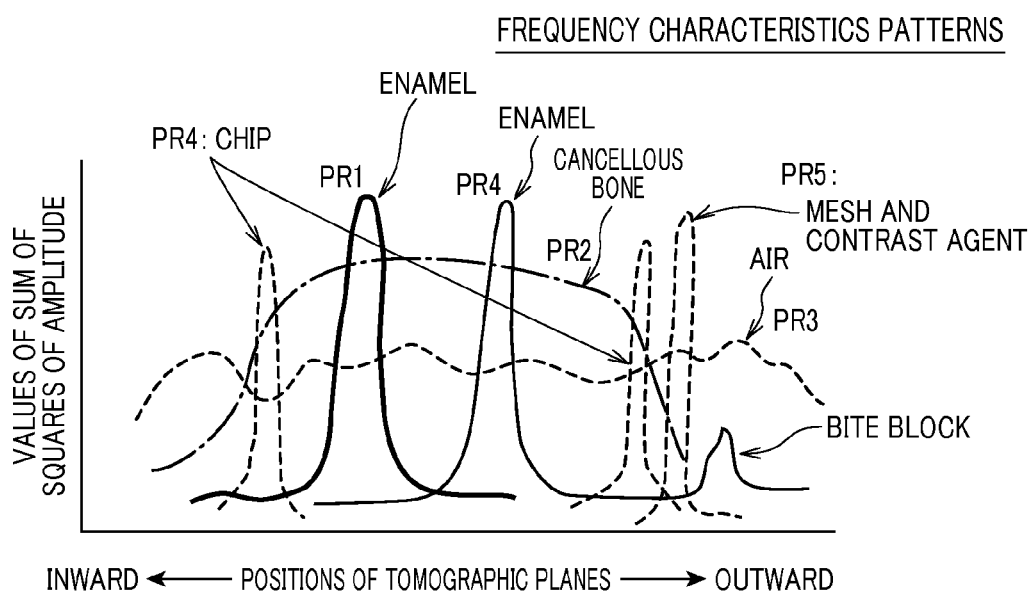
FIG. 31 is a view explaining profiles of frequency characteristics of various types of markers.

FIG. 30 shows, in its (B) and (C) sections, a state where the clip 70 is arranged at part of the tooth row of an object. The two chips 71 are fixedly arranged to be alternately on the front and rear sides of teeth (teeth row) such that the chips 71 differ in positions along the tooth row direction and pinch the gum with the help of the wire member 72. In this arrangement, the foregoing autofocus processing shown in FIG. 10 provides a three-dimensional understanding of the two chips 71 and produce two images, respectively, optimally focusing sections CR1 and CR2 which three dimensionally contain the respective chips 71 (refer to FIG. 30(C)). During this production, frequency characteristic patterns shown in FIG. 31 are adopted, in which two profiles PR4 each showing peaks of the frequency characteristics of the chips 71 appear on both sides of the frequency characteristic PR2 of the cancellous bone. The image processor 56 refers to the two profiles PR4 profile by profile to perform the reconstruction similarly to the foregoing embodiment. Hence, the three-dimensional positions P1real of the respective two chips 71 (P1'real; refer to FIGS. 20-22) and two optimally focused images (or partial images) of the sections CR1 and CR2 containing those positions can be provided.

In producing the two optimally focused images, it is able to understand positional information P from a distance $D_{BN}$ between the positions of the two chips 71 in the back and forth direction of the tooth row. And an amount of shift, $L_{BN}$, of the chips 71 in the lateral direction (that is, a direction along the tooth row) is also known from the design of the clips. Hence, the image processor 56 can calculate the thickness of the alveolar bone pinched by the two clips 71. In addition to diagnosing the alveolar bone, it is reliably select a sectional position to be observed of the alveolar bone in the thickness direction thereof.

Figure 32:
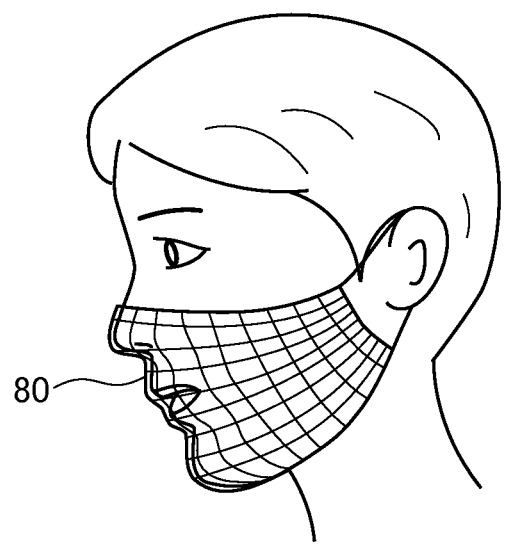
FIG. 32 is a view explaining a marker and how to use the marker, which is description of another modification.
Figure 33:
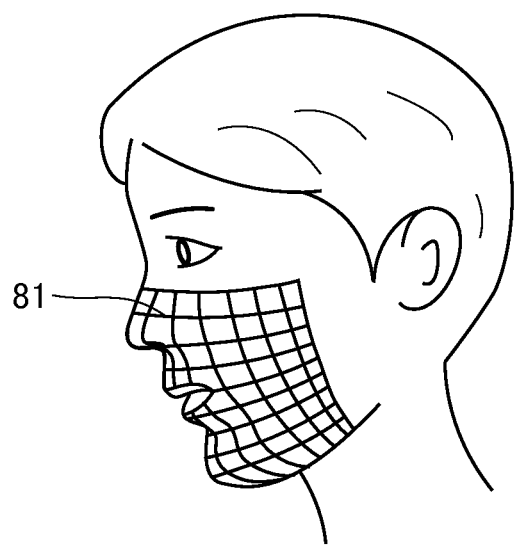
FIG. 33 is a view explaining a marker and how to use the marker, which is description of still another modification.

FIG. 32 shows another marker. This marker, which is used tightly cover the face of a patient being examined, is a mesh-like and expandable mask 80. This mask 80 is made of a wire material whose X-ray absorption factor differ from that of the oral cavity. Attaching the mask 80 tightly to the face is equivalent to draw grid lines on the face with the use of an X-ray maker. Simply these lines may be parallel with each other. Another example of this marker attached on the face is shown in FIG. 33, where an X-ray absorption material, such as barium, is applied to the face in a linear pattern or a grid pattern. A grid line 81 shown in FIG. 33 functions as a marker to the X-ray. Another marker applied to the face may be quick-drying cosmetic liquid with granular X-ray absorbent mixed therewith. This cosmetic liquid is applied to the face, so that the granular X-ray absorbent becomes a marker on the face The foregoing mesh-like marker 80, the marker 81 involving the application of the X-ray absorbent, and the granular marker provide a profile PR6 in the frequency characteristics, as shown in FIG. 31. The image processor 56 uses this profile PR6 to perform the foregoing auto-focusing reconstruction. As a result, there can be provided not only three-dimensional positions of the lines of the marker but also an optimally focused image taken along a surface of the three-dimensional positions, that is, an X-ray transmission image of the surface of the object's face. Displaying such an image on the foregoing 3D autofocus image in a superposed manner, an image which can in substitution for cepharometric images can be provided.

By the way, in the foregoing dental panoramic imaging apparatus, the pair of the X-ray and the detector may be installed on the ceiling. As an alternative, the apparatus can be mounted on an examination car or installed in a hose, if being compact in size and movable in structure.

The detector which can be employed in the radiation imaging apparatus of the present invention is not limited to the digital type of CdTe detector, but photon-counting type detectors can also be employed. Such photon-counting type detectors are known by for example Patent Publication JP-A-2004-325183.

The detector used by the radiation imaging apparatus according to the present invention is not always limited to use of the same type of detector. It is necessary to change an amount of energy of the X-ray depending on types of objects being imaged, so that material of the X-ray detecting elements may be selected in accordance with X-ray absorbing coefficients tuned to the necessary amount of X-ray energy. When it is necessary to generate larger amounts of energy, materials such as LaBr3, CdTe, CZT, and GOS can be adopted for the X-ray detecting elements. By contrast, for smaller amounts of X-ray energy, materials such as Si, CdTe, CZT, and CsI can be adopted for the X-ray detecting elements.

Further, the display mode is not limited to displaying the three-dimensional panoramic image (surface image). For example, from the profile in the tomographic plane positions versus the values of sums of squares of amplitude shown in FIG. 17, a width assumed to be focused can be obtained from the tomographic planes and the frequency characteristics, and using the width, the thicknesses of a tooth and/or the alveolar bone, that is, the thicknesses of those in the depth direction, can be measured. When a configuration to obtain this measurement information can be applied, together with the foregoing photon-counting type detector, to the alveolar bone close to the first false molar, bone mineral content can be measured quantitatively.

When the imaging according to the present invention is applied to the mandibular antra or portions close thereto in the oral cavity, it is possible to provide, to some extent, image information about the stereoscopic structure of the mandibular antra. Moreover, comparing a bilateral difference in the image makes it possible to detect inflammation in the mandibular antra (empyema) in a more accurate manner more than the conventional. Similarly, when the imaging according to the present invention is applied to the carotid artery or portions close thereto, calcification of the carotid artery, which is assumed to be one of the reasons for arterial sclerosis, can be clearly displayed three-dimensionally, providing more accurate diagnostic information compared to the conventional.

The radiation imaging apparatus according to the invention will not be limited to applications for the dental panoramic imaging apparatus, but can be put into practice in applications where the tomosynthesis technique is used to understand the three-dimensional shapes (positions) inside an object. Such applications include mammography using the tomosynthesis technique and an X-ray scanner for lung cancer in the medical field. Further, the radiation imaging apparatus according to the invention can be applied to nuclear medicine diagnosis apparatuses called emission CT (ECT) apparatuses such as a gamma camera and a SPECT apparatus. In this application, gamma-rays radiated from RI (radioisotope) administered into an object are acquired by a detector via a collimator with holes opened in a designated direction. In this case, the RI and the collimator compose the radiation emitting source.

In addition, the number of detectors mounted in the radiation imaging apparatus of the present invention is not always limited to one, but may be two or more. Such two or more detectors can be driven as one unit or in parallel in a modality.

The radiation imaging apparatus of the present invention can also be applied to industrial applications, which include acquiring information about contents of products or commodities carried by a belt conveyor and positions of such products or commodities, inspecting three-dimensional structures of a flexible substrate connected to a flat panel display, acquiring information about three-dimensional distributions and sizes of holes in a mold, and acquiring positional information of contents in baggage screening in the airport. Objects being imaged can be moved linearly, in a circle, in a curve or in other ways. That is, the 3D referential tomographic plane can be set as a tomographic plane or section which is flat, cylindrical, or curved.

In particular, in the foregoing industrial applications, an object being imaged is allowed to move relatively to the pair of the X-ray tube and the detector, if necessary. Further, some reasons in the mechanical design permit only the detector to be moved relatively to an object being imaged or a patient and the radiation source.

INDUSTRIAL APPLICABILITY

According to the present invention, it is possible to provide a radiation imaging technique which is able to optimally focus on the entire region of an object being imaged in a three-dimensional panoramic image in a state where the actual state (position and shape) of the object is three-dimensionally depicted with higher accuracy and distortion due to changes in the enlargement factor is removed or reduced well, thus providing higher industrial availability.

DESCRIPTION OF REFERENCE NUMBERS

1 Dental panoramic imaging apparatus (radiation imaging apparatus)
12 Control & calculation apparatus
14 Imaging unit
31 X-ray tube (radiation tube)
32 Detector
33 Collimator
41 High-voltage generator
53 Buffer memory
54 Image memory
55 Frame memory
56 Image processor
57 Controller
58 Operation device
60 Monitor
61 ROM

What is claimed is:
1. A radiation imaging apparatus comprising:
a radiation source that emits a radiation;
a radiation detector that outputs, frame by frame, digital-quantity two-dimensional data corresponding to incidence of the radiation thereto;
moving means for moving a pair of the radiation source and the radiation detector such that the radiation is scanned to focus on a desired referential tomographic plane of the object, the radiation source and the radiation detector being arranged to be opposed to each other with the object located therebetween;
data acquiring means for acquiring, frame by frame, the digital-quantity two-dimensional data outputted from the radiation detector while the pair of the radiation source and the radiation detector is moved relative to the object; and
image producing means for producing a three-dimensional optimally focused image based on the data acquired by the data acquiring means, a portion to be imaged of the object in the three-dimensional optically focused image being optimally focused and reflecting an actual size and shape of the portion thereon;
wherein the image producing means comprises:
referential-plane image reconstructing means for reconstructing, as a referential-plane image, a projection image based on the data acquired by the data acquiring means, the projection image being produced by projecting the referential tomographic plane onto a detection surface of the radiation detector, and optimally-focused image producing means for producing the three-dimensional optimally focused image based on data of the referential-plane image and the frame by frame data.

2. The radiation imaging apparatus of claim 1, wherein
the radiation source is an X-ray tube radiating X-rays as the radiation,
the radiation detector is a detector to detect the X-rays,
the referential tomographic plane is a three-dimensional (3D) referential tomographic plane which is curved and rectangular in a real space,
the portion being imaged of the object is a tooth row of a patient, and
the referential-plane image reconstructing means is configured to reconstruct a panoramic image of the tooth row.

3. The radiation imaging apparatus of claim 2, wherein
the optimally-focused image producing means comprises:
tomographic plane setting means for setting a plurality of tomographic planes along the 3D referential tomographic plane in a direction opposed to the 3D referential tomographic plane,
pixel value calculating means for calculating pixel values of each of the plurality of tomographic planes,
position identifying mean for identifying optimally focused sampling points of the portion being imaged based on image data of both the 3D referential tomographic plane and the plurality of tomographic planes to which the pixel value calculating means provides the pixel values,
pixel value providing means for providing the sampling points identified by the position identifying means, with pixel values based on the pixel values at the sampling points corresponding to the panoramic image and being present in a viewing direction from the X-ray tube to the detector via the respective sampling points,
tooth row deciding means for deciding the tooth row by recognizing the 3D referential tomographic plane provided at the sampling points to which the pixel values are provided by the pixel value providing means and a characteristic pattern shown by pixel values of the plurality of tomographic planes, and
noise removing means for removing noise from the sampling points of the tooth row decided by the tooth row deciding means.

4. The radiation imaging apparatus of claim 3, wherein the noise removing means comprises:
classification means for classifying substances every characteristic shown by the same type of substance based on the frequency characteristic at the respective sampling points, and
smoothing means for smoothly connecting each substance classified by the classification means.

5. The radiation imaging apparatus of claim 2, wherein the apparatus comprises:
panoramic image displaying means for displaying the panoramic image of the 3D referential tomographic plane, which is reconstructed by the referential-plane image reconstructing mean;
ROI setting means for enabling an operator to set a ROI (region of interest) on the panoramic image displayed by the panoramic image displaying means; and
partial image displaying means for clipping an image of the region set by the ROI, from the panoramic image and displaying the clipped image.

6. The radiation imaging apparatus of claim 2, wherein the apparatus comprises:
optimally-focused image displaying means for displaying the optimally focused image produced by the optimally-focused image producing means;
production means for producing a panoramic image by projecting the optimally focused image onto the curved 3D referential tomographic plane along the viewing direction when it is desired to enable an operator to set a ROI (region of interest) on the optimally focused image displayed by the optimally-focused image displaying means;
ROI setting means for enabling the operator to set the ROI (region of interest) on the panoramic image produced by the production means; and
partial image displaying means for clipping an image of the region set by the ROI, from the panoramic image and displaying the clipped image.

7. The radiation imaging apparatus of claim 6, wherein the partial image displaying means is configured to display the clipped image in a template positionally imitating the tooth row.

8. The radiation imaging apparatus of claim 2, wherein the apparatus comprises:
optimally-focused image displaying means for displaying the optimally focused image produced by the optimally-focused image producing means;
production means for producing a panoramic image by projecting the optimally focused image to a two-dimensional tomographic plane along the viewing direction when it is desired to enable an operator to set a ROI (region of interest) on the optimally focused image displayed by the optimally-focused image displaying means;
ROI setting means for enabling the operator to set the ROI (region of interest) on the panoramic image produced by the production means; and
partial image displaying means for clipping an image of the region set by the ROI, from the panoramic image and displaying the clipped image.

9. The radiation imaging apparatus of claim 2, wherein the apparatus comprises
three-dimensional display means for three-dimensionally displaying at least one of the panoramic image reconstructed by the referential-plane image reconstructing means and the optimally-focused image produced by the optimally-focused image producing means.

10. The radiation imaging apparatus of claim 9, wherein the three-dimensional display means is configured to be able to display at least the one of the panoramic image and the optimally focused image through at least of one of rotation and movement modes.

11. The radiation imaging apparatus of claim 1, wherein
the desired referential tomographic plane is, partially or as a whole, a desired three-dimensional section of the object which is produced from a surface image imaged by a camera, the desired three-dimensional section of the object which is imaged by a medical modality including an MRI (magnetic resonance imaging) apparatus, a CT (computed tomography) scanner, or an ultrasound diagnostic apparatus, or the desired three-dimensional section of the object is set based on three-dimensional data of the object imaged by the medical modality.

12. The radiation imaging apparatus of claim 1, wherein
the radiation imaging apparatus includes a marker,
the object is an oral cavity of a patient being examined, the data acquiring means is configured to acquire the digital-quantity two-dimensional data during drive of the moving means in a state where the marker made of radiation absorbing material is arranged at the oral cavity, and the optimally-focused image producing means is configured to recognize a three-dimensional position of the marker and produce an image focusing the three-dimensional position recognized with the marker.

13. A data processing apparatus processing data outputted from a system, the system comprising:
a radiation source that emits a radiation;
a radiation detector that output, frame by frame, digital-quantity two-dimensional data corresponding to incidence of the radiation thereto;
moving means for moving a pair of the radiation source and the radiation detector such that the radiation is scanned to focus on a desired referential tomographic plane of the object, the radiation source and the radiation detector being arranged to be opposed to each other with the object located therebetween; and
data acquiring means for acquiring, frame by frame, the digital-quantity two-dimensional data outputted from the radiation detector while the pair of the radiation source and the radiation detector, the radiation detector, or the object is moved relative to the object,
the data processing apparatus comprising:
data storing means for receiving and storing therein the digital-quantity two-dimensional data; and
image producing means for producing a three-dimensional optimally focused image based on the digital-quantity two-dimensional data stored in the data storing means, a portion to be imaged of the object being imaged to be optimally focused and to reflect an actual size and shape of the portion thereon;
wherein the image producing means comprises:
referential-plane image reconstructing means for reconstructing, as a referential-plane image, a projection image based on the digital-quantity two-dimensional data stored in the data storing means, the projection image being produced by projecting the referential tomographic plane to a detection surface of the radiation detector, and
optimally-focused image producing means for producing the three-dimensional optimally focused image based on data of the referential-plane image.

14. The data processing apparatus of claim 13, wherein
the system is a dental panoramic imaging apparatus provided with an X-ray tube that composes the radiation source and radiates X-rays serving as the radiation, and a detector that composes the radiation detector and detects the X-rays, wherein the referential tomographic plane is given as a curved three-dimensional (3D) referential tomographic plane present in a real space and the portion being imaged of the object is a tooth row of a patient;
the optimally-focused image producing means comprises:
tomographic plane setting means for setting a plurality of tomographic planes along the 3D referential tomographic plane in a direction opposed to the 3D referential tomographic plane,
pixel value calculating means for calculating pixel values of each of the plurality of tomographic planes,
position identifying mean for identifying optimally focused sampling points of the portion being imaged based on image data of both the 3D referential tomographic plane and the plurality of tomographic planes to which the pixel value calculating means provides the pixel values,
pixel value providing means for providing the sampling points identified by the position identifying means, with pixel values based on the pixel values at the sampling points corresponding to the panoramic image and being present in a viewing direction from the X-ray tube to the detector via the respective sampling points,
tooth row deciding means for deciding the tooth row by recognizing the 3D referential tomographic plane provided at the sampling points to which the pixel values are provided by the pixel value providing means and a characteristic pattern shown by pixel values of the plurality of tomographic planes, and
noise removing means for removing noise from the sampling points of the tooth row decided by the tooth row deciding means.

15. The data processing apparatus of claim 14, wherein the noise removing means comprises:
classification means for classifying substances every characteristic shown by the same type of substance based on the frequency characteristic at the respective sampling points, and
smoothing means for smoothly connecting each substance classified by the classification means.

16. A method of imaging using a radiation, comprising steps of:
acquiring data, frame by frame, outputted from a radiation detector while a pair of a radiation source and the radiation detector is moved relative to the object, the radiation detector outputting, frame by frame, digital-quantity two-dimensional data corresponding to incidence of the radiation thereto; and
producing a three-dimensional optimally focused image based on the digital-quantity two-dimensional data acquired by the acquiring step, a portion to be imaged of the object in the three-dimensional optically focused image being optimally focused and reflecting an actual size and shape of the portion therein;
the producing step includes steps of:
reconstructing, as a referential-plane image, a projection image produced by projecting a desired referential tomographic plane of a portion being imaged of the object to a detection surface of the radiation detector based on the data acquired at the acquiring step;
setting a plurality of tomographic planes along the 3D referential tomographic plane in a direction opposed to the 3D referential tomographic plane;
calculating pixel values of each of the plurality of tomographic planes based on pixel values of the referential tomographic plane;
identifying optimally focused sampling points of the portion being imaged based on image data of both the 3D referential tomographic plane and the plurality of tomographic planes to which the pixel values are provided;
providing the identified sampling points with pixel values based on the pixel values at the sampling points corresponding to the panoramic image and being present in a viewing direction from the radiation source to the radiation detector via the respective sampling points;
deciding the portion being imaged, by recognizing the 3D referential tomographic plane provided at the sampling points to which the pixel values are provided and a characteristic pattern shown by pixel values of the plurality of tomographic planes; and removing noise from the sampling points of the decided portion being imaged.

17. A computer-readable program stored in a non-transitory computer readable memory and produced to enable a computer to process data outputted from a system comprising:

a radiation source that emits a radiation;

a radiation detector that output, frame by frame, digital-quantity two-dimensional data corresponding to incidence of the radiation thereto;

moving means for moving a pair of the radiation source and the radiation detector such that the radiation is scanned to focus on a desired referential tomographic plane of the object, the radiation source and the radiation detector being arranged to be opposed to each other with the object located therebetween; and data acquiring means for acquiring, frame by frame, the digital-quantity two-dimensional data outputted from the radiation detector while the pair of the radiation source and the radiation detector is moved relative to the object, wherein the computer-readable program enables the computer to have functions realized by the steps of:

reconstructing, as a referential-plane image, a projection image produced by projecting a desired referential tomographic plane of a portion being imaged of the object to a detection surface of the radiation detector based on the digital-quantity two-dimensional data acquired;

setting a plurality of tomographic planes along a 3D referential tomographic plane in a direction opposed to the 3D referential tomographic plane;

calculating pixel values of each of the plurality of tomographic planes based on pixel values of the referential tomographic plane;

identifying optimally focused sampling points of the portion being imaged based on image data of both the 3D referential tomographic plane and the plurality of tomographic planes to which the pixel values are provided;

providing the identified sampling points with pixel values based on the pixel values at the sampling points corresponding to the panoramic image and being present in a viewing direction from the radiation source to the radiation detector via the respective sampling points;

deciding the portion being imaged, by recognizing the 3D referential tomographic plane provided at the sampling points to which the pixel values are provided and a characteristic pattern shown by pixel values of the plurality of tomographic planes;

removing noise from the sampling points of the decided portion being imaged; and producing a three-dimensional optimally focused image including the portion being imaged with an actual size and shape of the portion reflected thereon, by connecting the sampling points of the portion from which the noise is removed.

* * * * *